United States Patent
Houser

(10) Patent No.: US 11,653,944 B2
(45) Date of Patent: *May 23, 2023

(54) PASSIVE DISSECTION FEATURES FOR ULTRASONIC SURGICAL INSTRUMENT

(71) Applicant: Cilag GmbH International, Zug (CH)

(72) Inventor: Kevin L. Houser, Springboro, OH (US)

(73) Assignee: Cilag GmbH International, Zug (CH)

( * ) Notice: Subject to any disclaimer, the term of this patent is extended or adjusted under 35 U.S.C. 154(b) by 739 days.

This patent is subject to a terminal disclaimer.

(21) Appl. No.: 16/696,271

(22) Filed: Nov. 26, 2019

(65) Prior Publication Data

US 2020/0163691 A1    May 28, 2020

Related U.S. Application Data

(63) Continuation of application No. 15/158,769, filed on May 19, 2016, now Pat. No. 10,543,013.

(51) Int. Cl.
*A61B 17/32* (2006.01)

(52) U.S. Cl.
CPC ........... *A61B 17/320092* (2013.01); *A61B 2017/320094* (2017.08); *A61B 2017/320095* (2017.08)

(58) Field of Classification Search
CPC ........ A61B 17/320092; A61B 17/2812; A61B 17/282; A61B 2017/320094; A61B 2017/320095; A61B 2017/2945; A61B 2017/2825; A61B 2017/00738; A61B 2090/08021
See application file for complete search history.

(56) References Cited

U.S. PATENT DOCUMENTS

| 5,322,055 A | 6/1994 | Davison et al. |
| 5,873,873 A | 2/1999 | Smith et al. |
| 5,980,510 A | 11/1999 | Tsonton et al. |

(Continued)

FOREIGN PATENT DOCUMENTS

| CN | 101820825 A | 9/2010 |
| EP | 0 695 535 A1 | 2/1996 |

(Continued)

OTHER PUBLICATIONS

Chinese Search Report dated Nov. 21, 2020 for Application No. CN 201780030999.6, 3 pgs.

(Continued)

*Primary Examiner* — Toan M Le
(74) *Attorney, Agent, or Firm* — Frost Brown Todd LLP

(57) ABSTRACT

An apparatus for operating on tissue includes a body assembly, a shaft, an acoustic waveguide, and an end effector. The end effector includes an ultrasonic blade, a clamp arm, and a blade guard. The ultrasonic blade is in acoustic communication with the waveguide. The clamp arm is configured to pivot toward and away from the ultrasonic blade. The clamp arm has a first tine. The blade guard extends from the shaft. The blade guard has a longitudinally extending arm defining a concave pathway and a second tine located distal to the longitudinally extending arm. The ultrasonic blade is partially housed within the concave pathway. The first tine and the second tine are configured to grasp tissue when the clamp arm pivots toward the ultrasonic blade.

20 Claims, 31 Drawing Sheets

(56) References Cited

U.S. PATENT DOCUMENTS

| | | | |
|---|---|---|---|
| 6,325,811 B1 | 12/2001 | Messerly | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,247,953 B2 | 2/2016 | Palmer et al. | |
| 9,381,058 B2 | 7/2016 | Houser et al. | |
| 9,393,037 B2 | 7/2016 | Olson et al. | |
| 9,895,161 B2 | 2/2018 | Messerly et al. | |
| 10,543,013 B2* | 1/2020 | Houser | A61B 17/320092 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0167671 A1* | 7/2008 | Giordano | A61B 17/07207 606/167 |
| 2008/0200940 A1 | 8/2008 | Eichmann et al. | |
| 2012/0116265 A1 | 5/2012 | Houser et al. | |
| 2015/0080925 A1 | 3/2015 | Schulte et al. | |
| 2015/0148834 A1 | 5/2015 | Gee et al. | |
| 2015/0148835 A1 | 5/2015 | Faller et al. | |

FOREIGN PATENT DOCUMENTS

| | | | |
|---|---|---|---|
| EP | 0 908 149 A1 | 4/1999 | |
| EP | 1 510 178 A1 | 3/2005 | |
| JP | 2004-337187 A | 12/2004 | |
| WO | WO 2005-076968 A2 | 8/2005 | |
| WO | WO 2012/135721 A1 | 10/2012 | |
| WO | WO 2014/004120 A1 | 1/2014 | |

OTHER PUBLICATIONS

European Search Report, Extended, and Written Opinion dated May 21, 2021 for Application No. EP 21151478.1, 8 pgs.

Japanese Office Action, Notice of Reasons for Refusal, dated May 11, 2021 for Application No. JP 2018-560458, 8 pgs.

European Examination Report dated Nov. 6, 2019 for Application No. 17725096.6, 5 pages.

International Search Report and Written Opinion dated Nov. 13, 2017 for International Application No. PCT/US2017/032315, 13 pages.

U.S. Appl. No. 61/410,603, filed Nov. 5, 2010.

\* cited by examiner

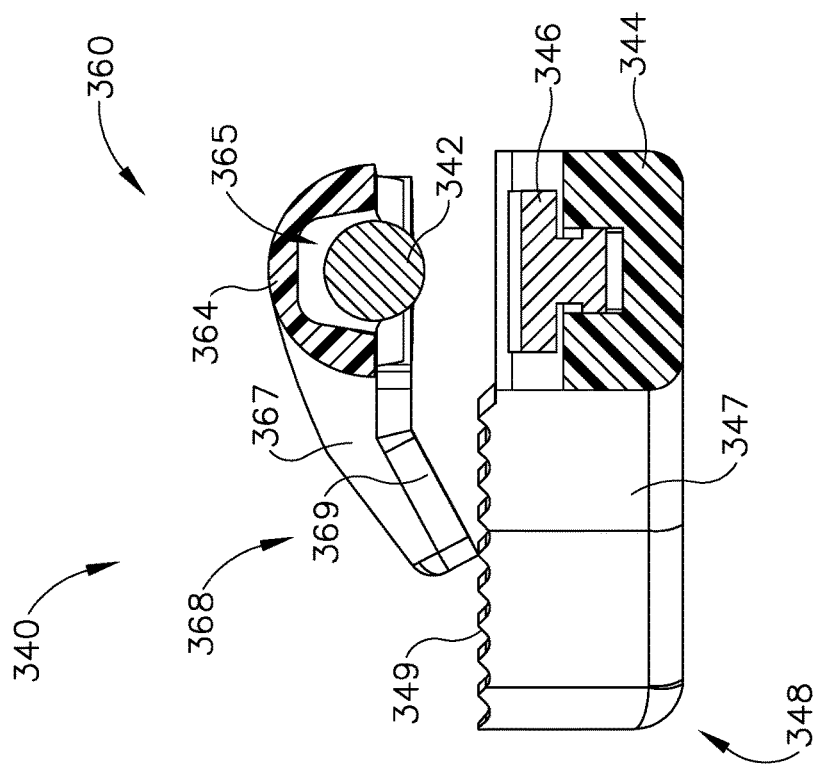
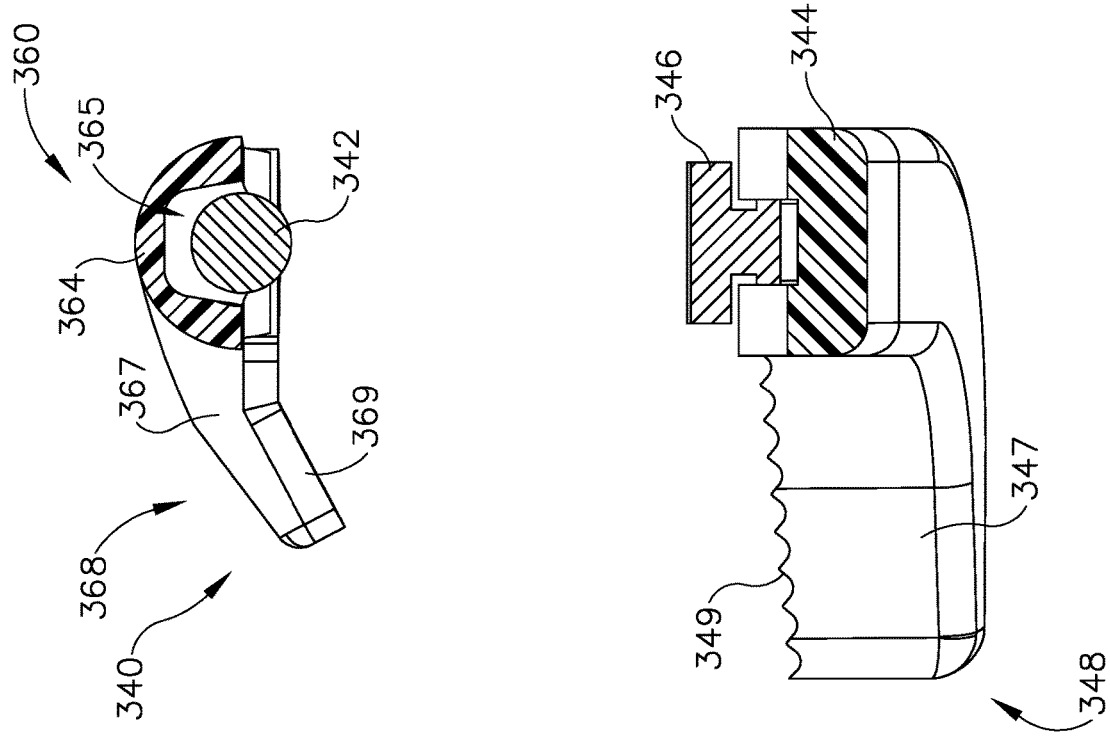
Fig.11B
Fig.11A

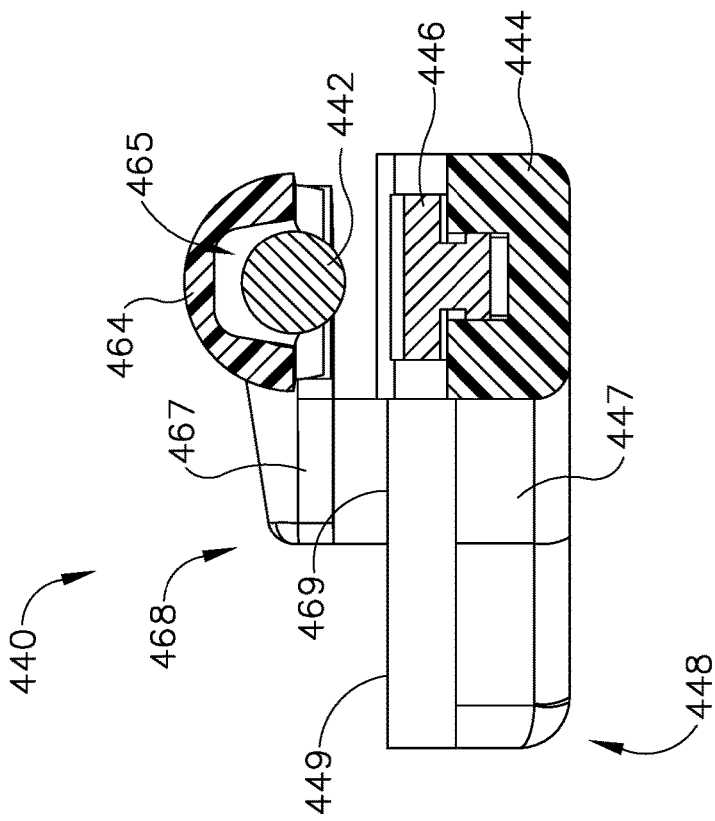
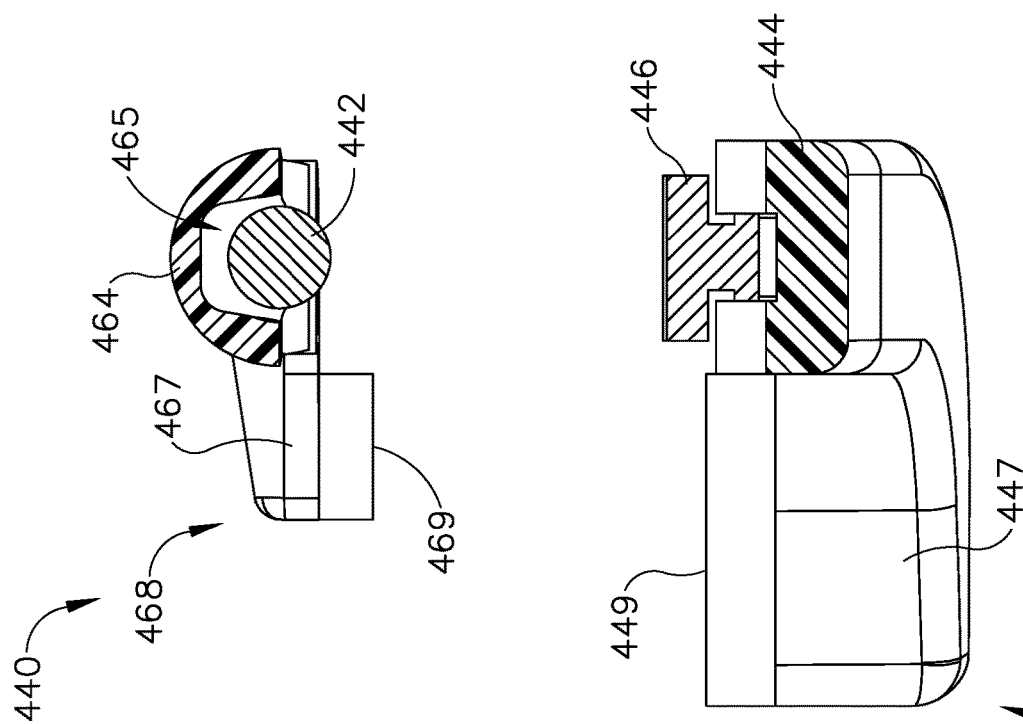
Fig.13B
Fig.13A

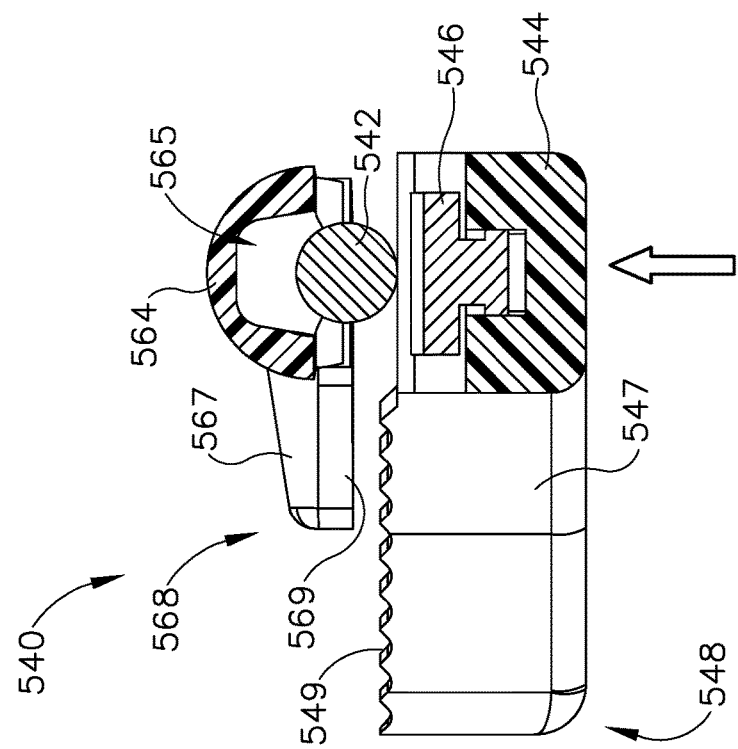
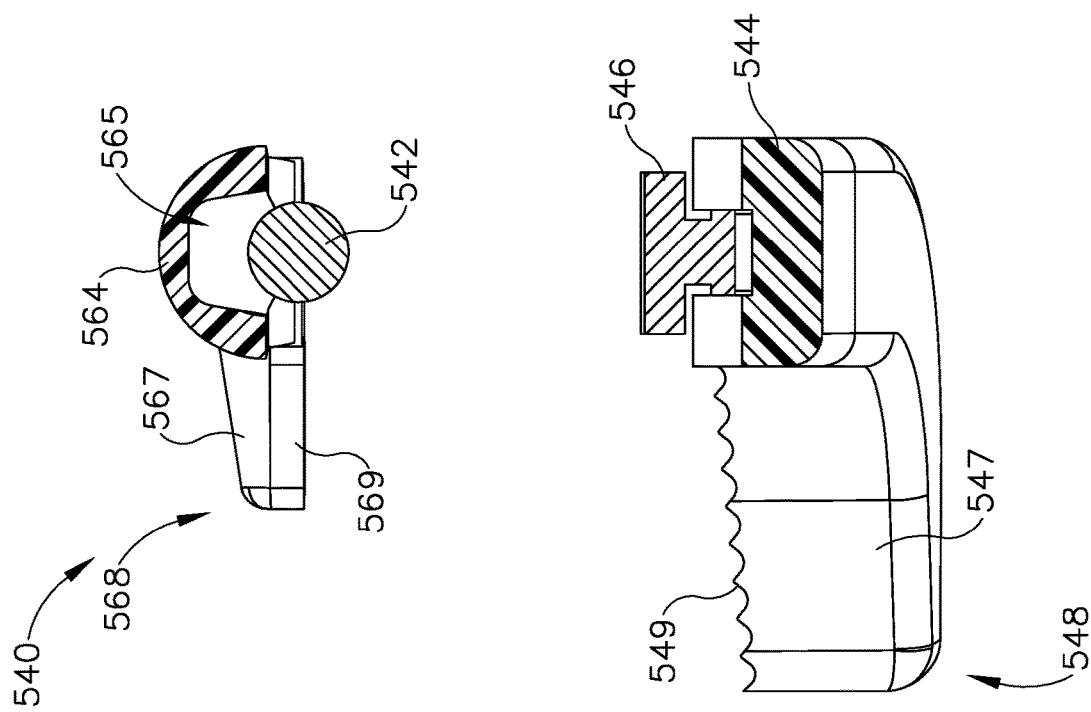
Fig.15B
Fig.15A

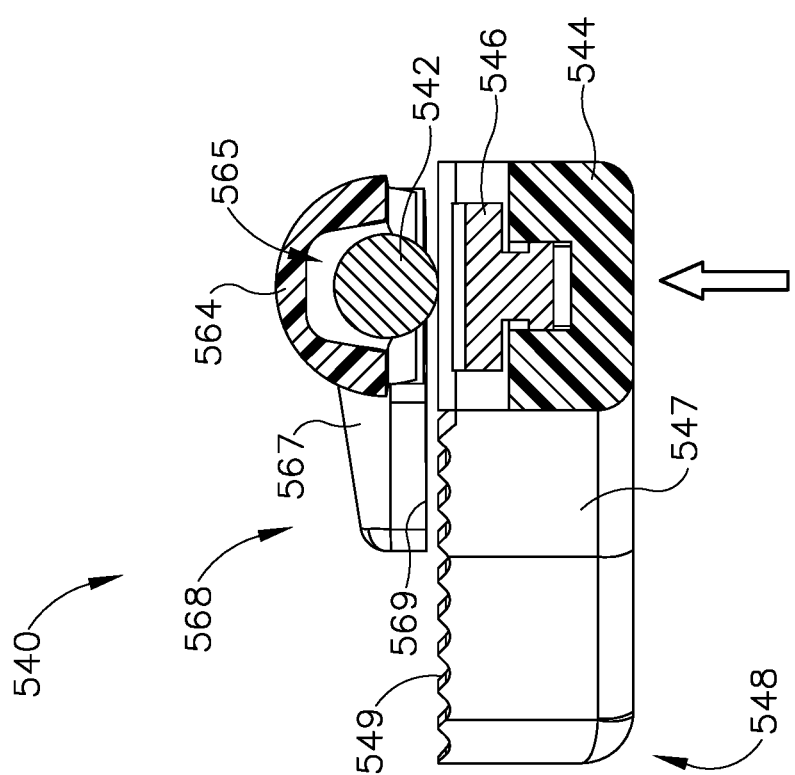

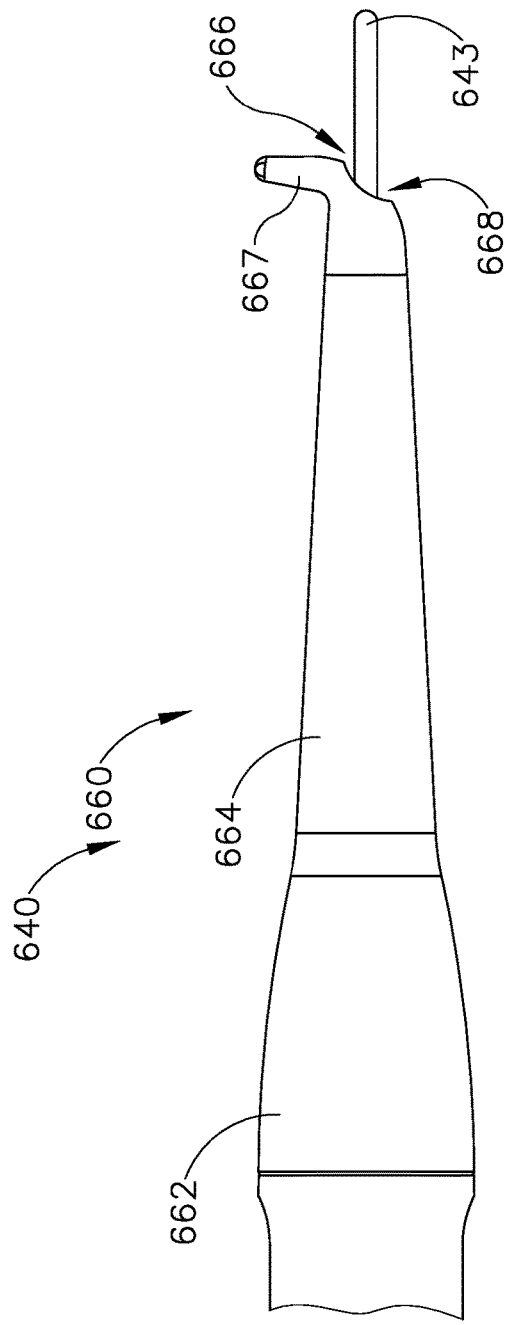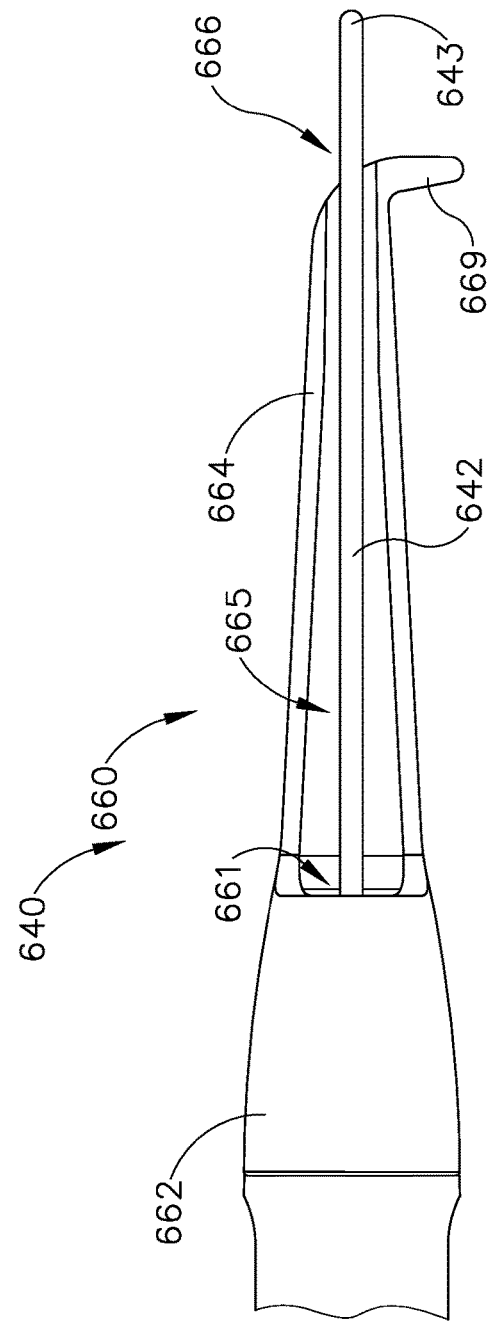

US 11,653,944 B2

PASSIVE DISSECTION FEATURES FOR ULTRASONIC SURGICAL INSTRUMENT

This application is a continuation of U.S. patent application Ser. No. 15/158,769, entitled "Passive Dissection Features for Ultrasonic Surgical Instrument," filed May 19, 2016, and published as U.S. Pub. No. 2017/0333072 on Nov. 23, 2017.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 11A depicts a cross-sectional rear view of the end effector of FIG. 10A, taken along line 11A-11A of FIG. 10A, where the end effector is in the open configuration as shown in FIG. 10A;

FIG. 11B depicts a cross-sectional rear view of the end effector of FIG. 10A, taken along line 11B-11B of FIG. 10B, where the end effector is in the first closed configuration as shown in FIG. 10B;

Figure 1:
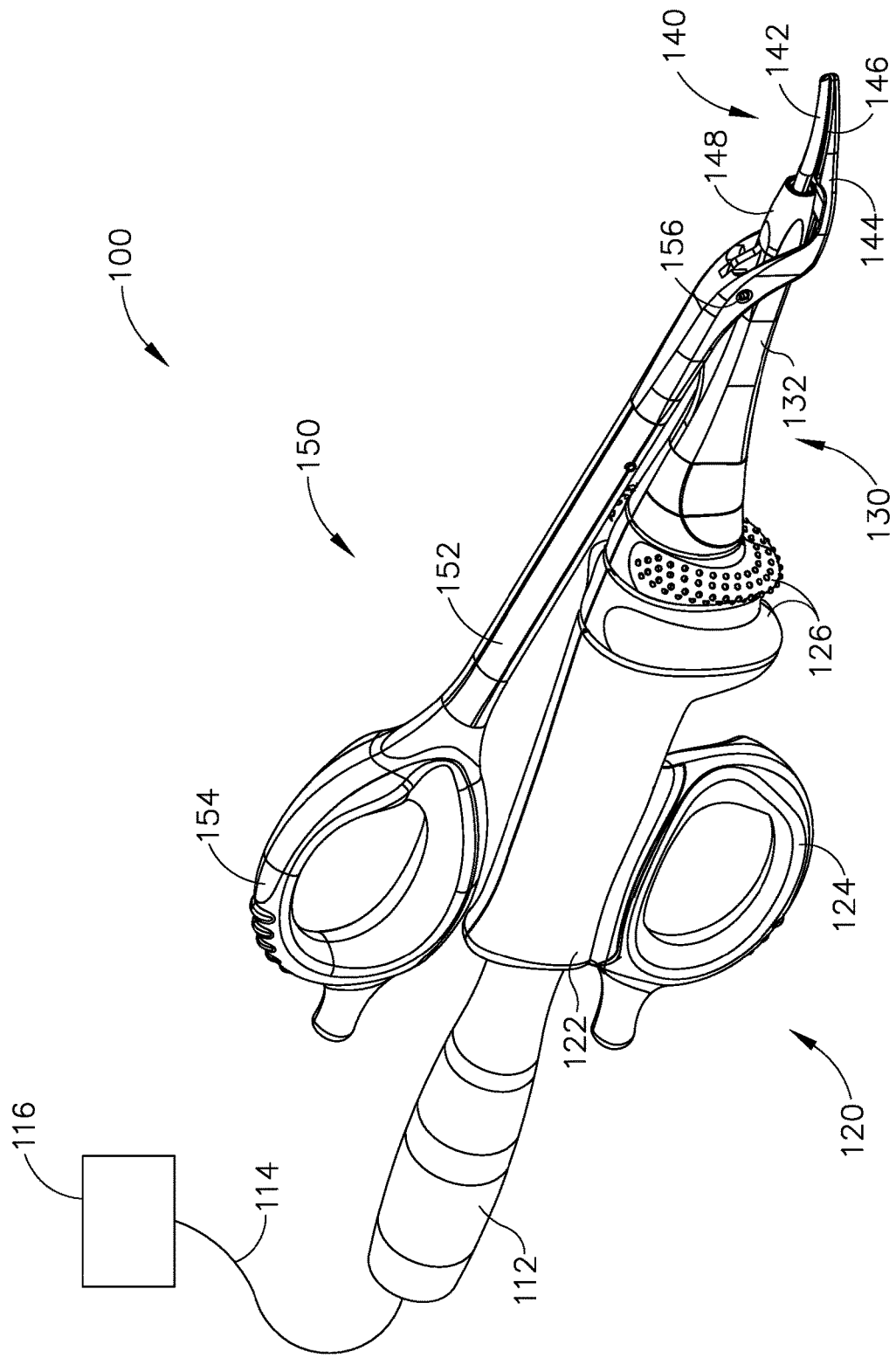
FIG. 1 depicts a perspective view of an exemplary ultrasonic surgical instrument.
Figure 4:
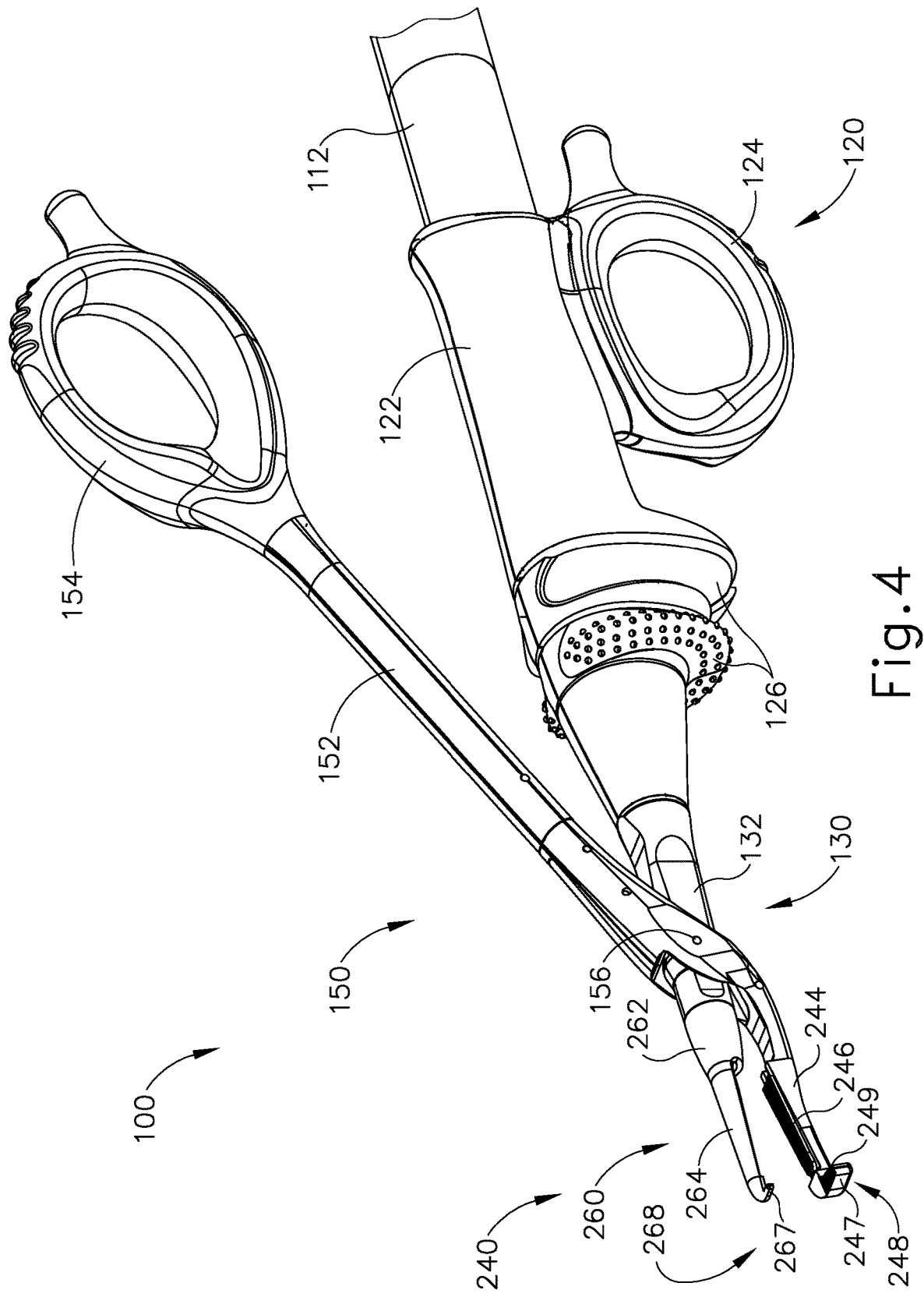
FIG. 4 depicts a perspective view of the surgical instrument of FIG. 1 with an exemplary alternative end effector.
Figure 12A:
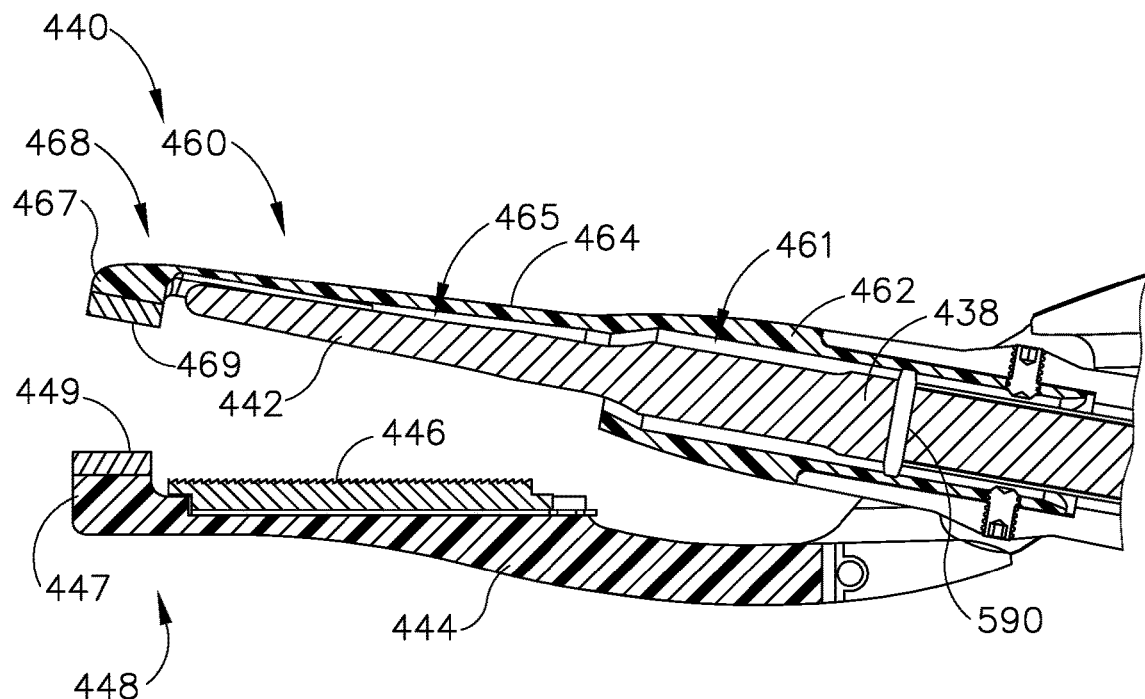
FIG. 12A depicts a cross-sectional side view of another alternative end effector that may be readily incorporated into the surgical instrument of FIG. 1, where the end effector is in an open configuration.
Figure 12B:
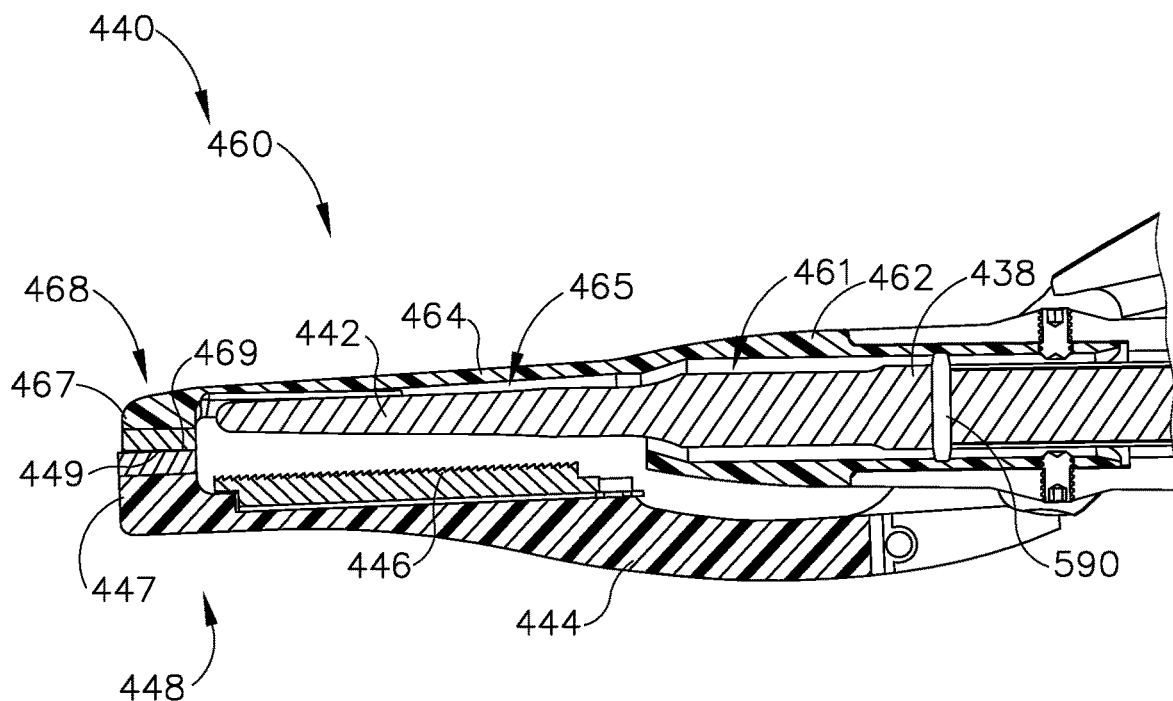
FIG. 12B depicts a cross-sectional side view of the end effector of FIG. 12A, where the end effector is in a first closed configuration.
Figure 12C:
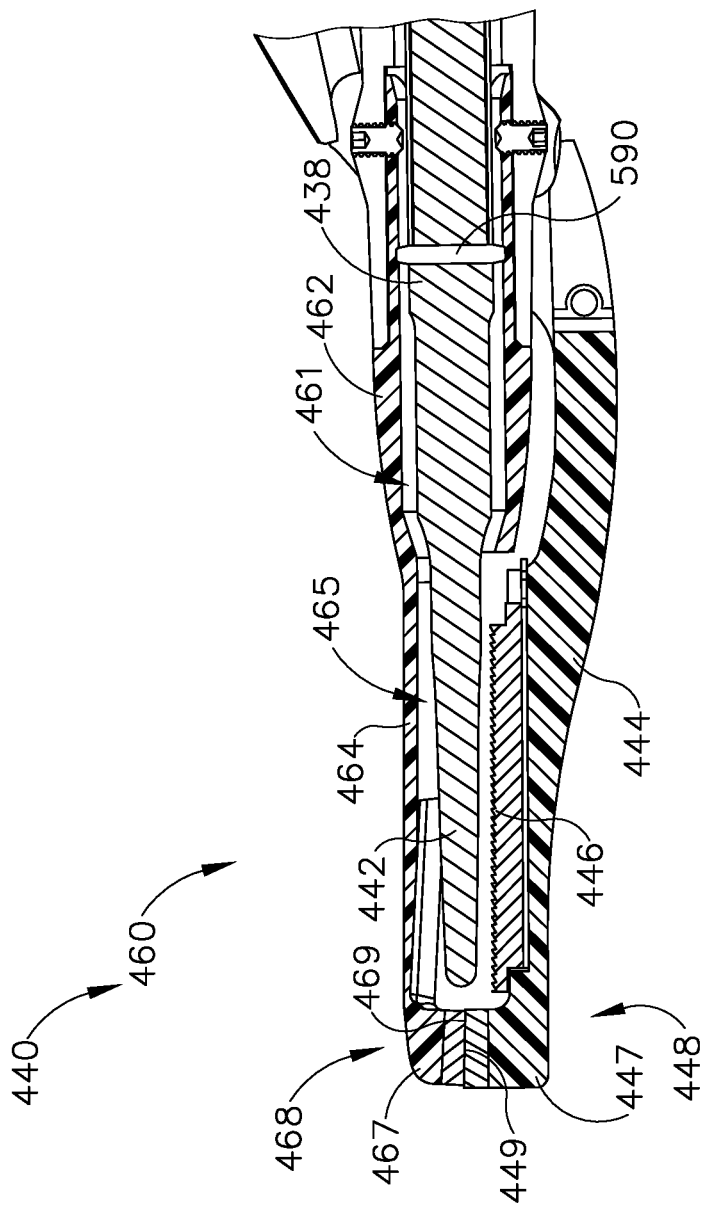
FIG. 12C depicts a cross-sectional side view of the end effector of FIG. 12A, where the end effector is in a second closed configuration.
Figure 13C:
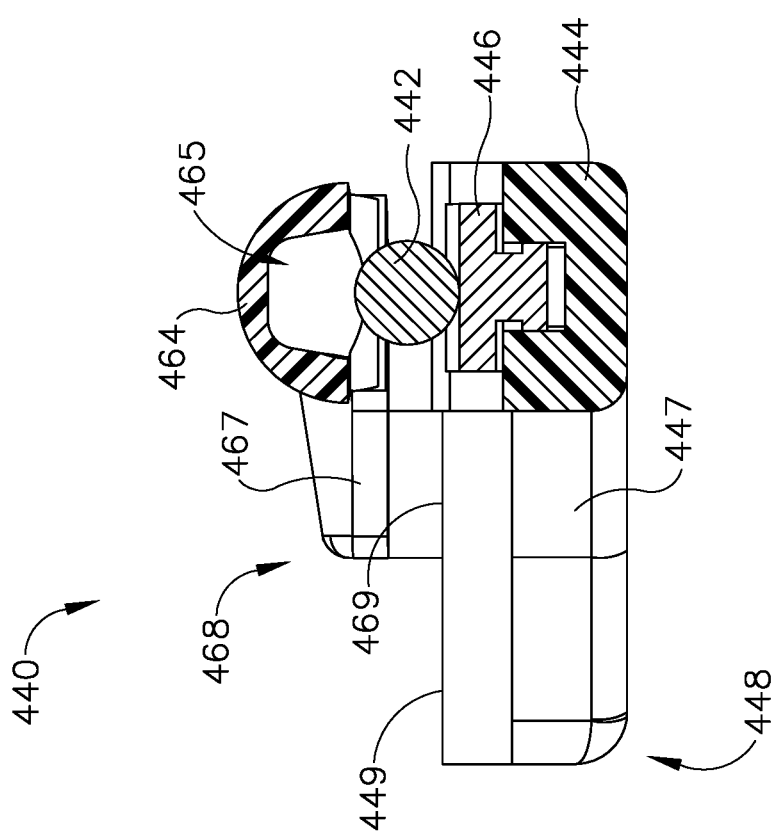
FIG. 13A depicts a cross-sectional rear view of the end effector of FIG. 12A, where the end effector is in the open configuration as shown in FIG. 12A.
FIG. 13B depicts a cross-sectional rear view of the end effector of FIG. 12A.
Figure 14A:
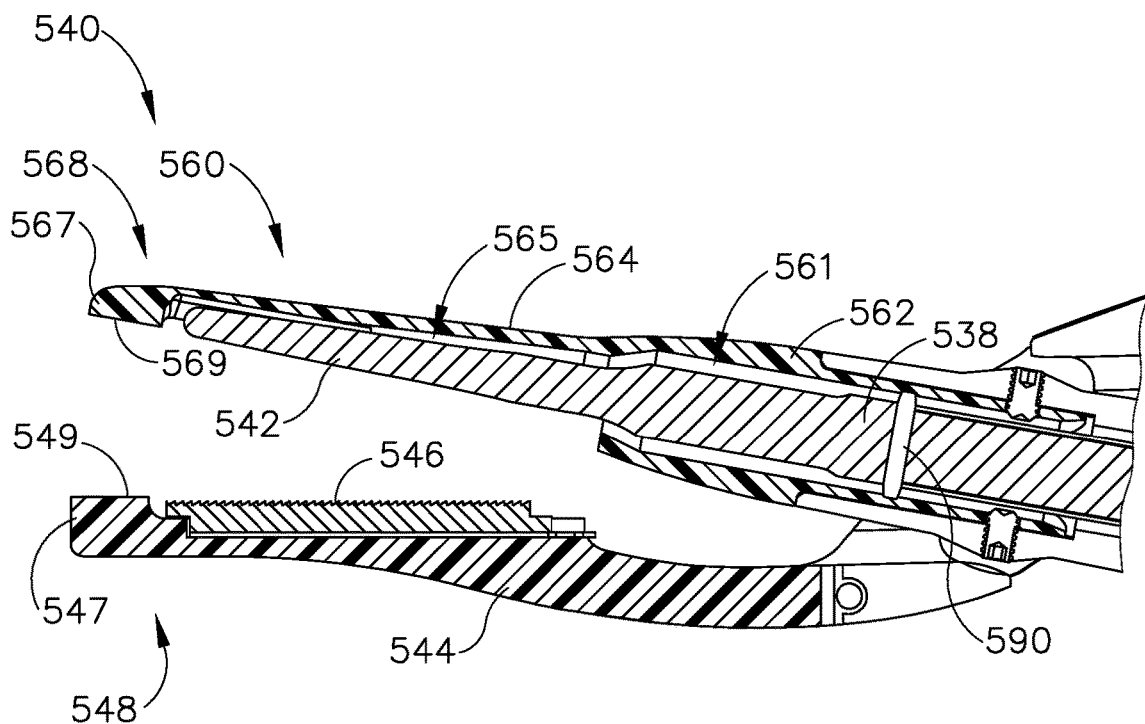
Figure 14B:
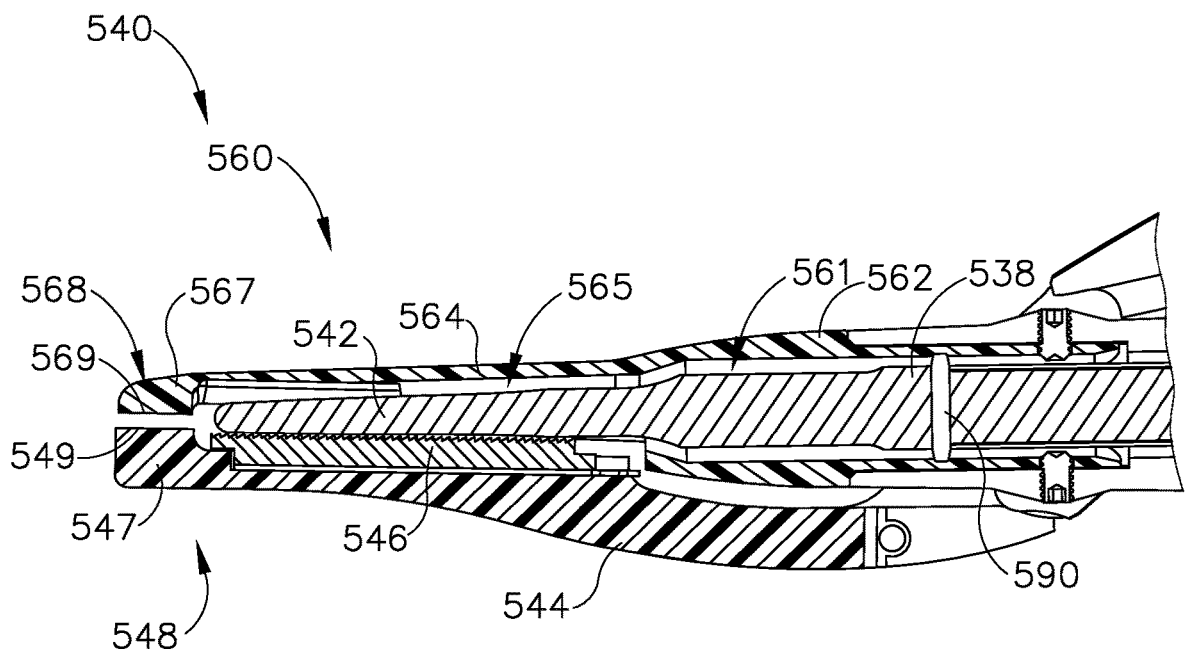
Figure 14C:
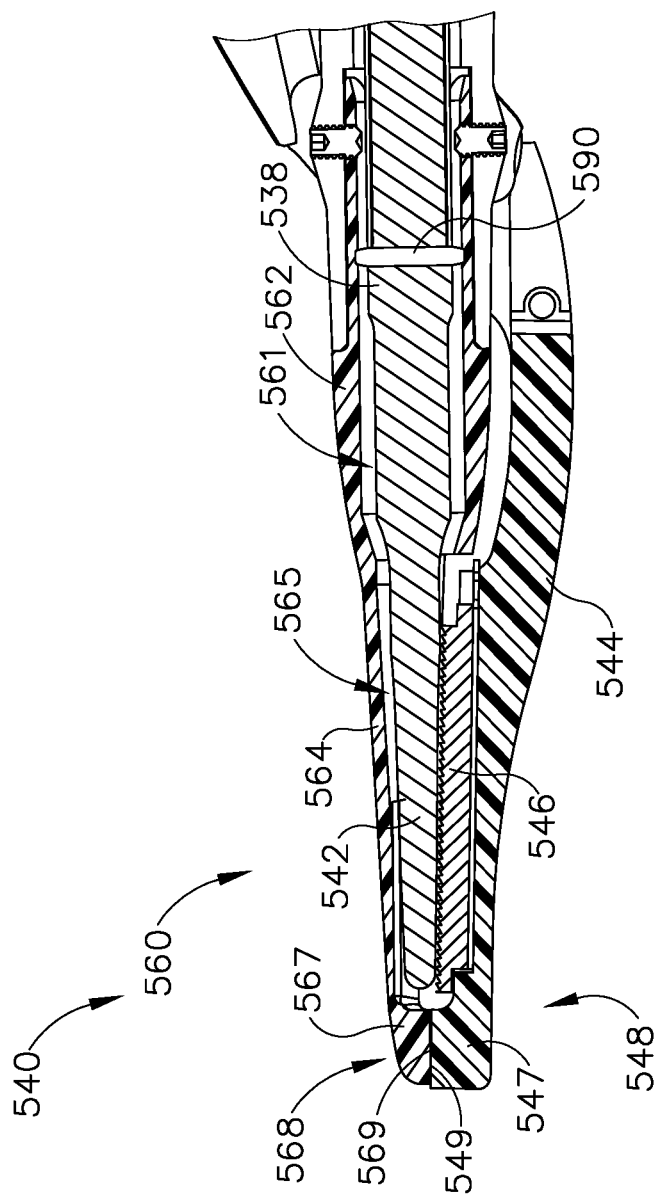
Figure 16A:
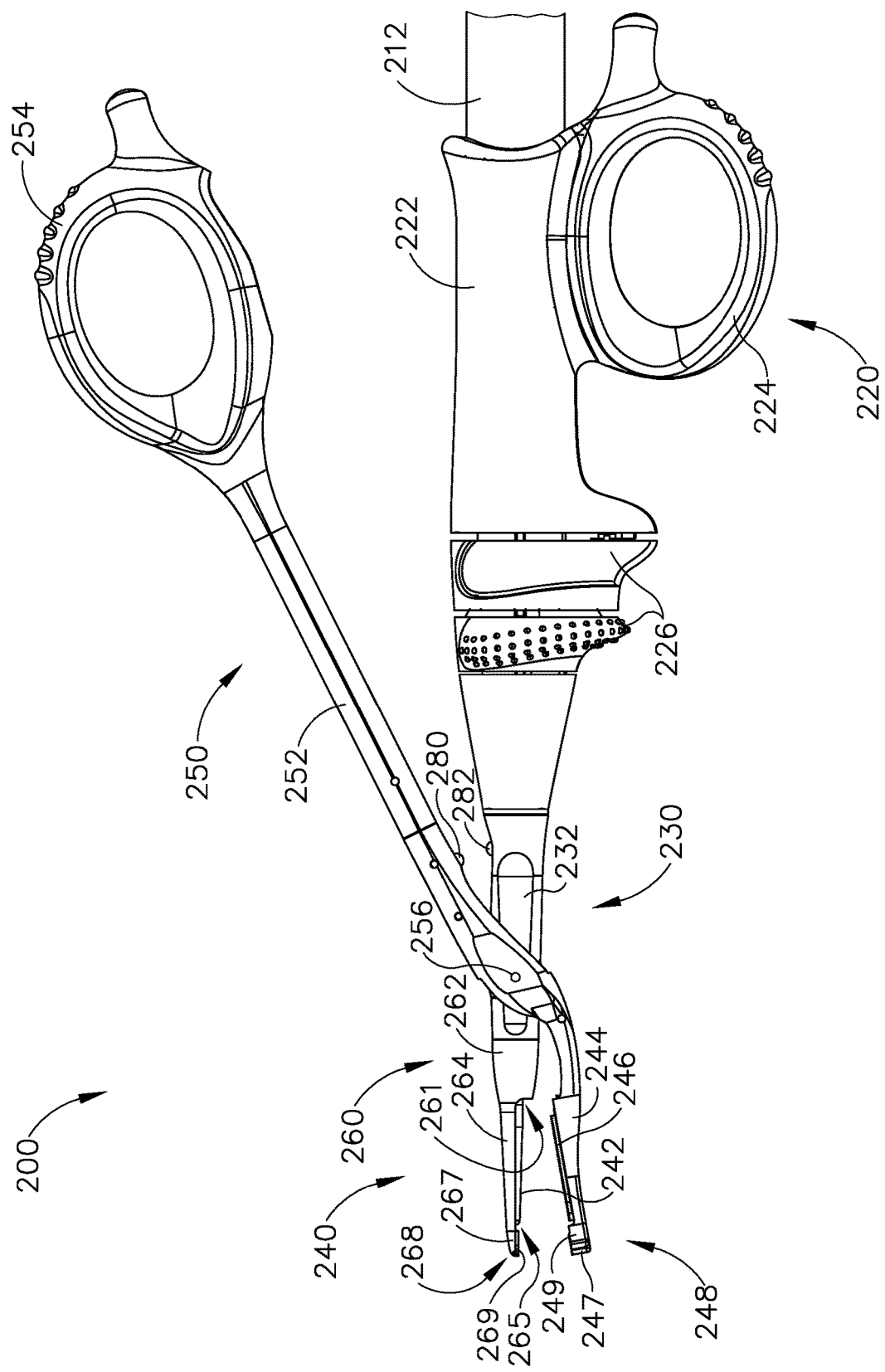
Figure 16B:
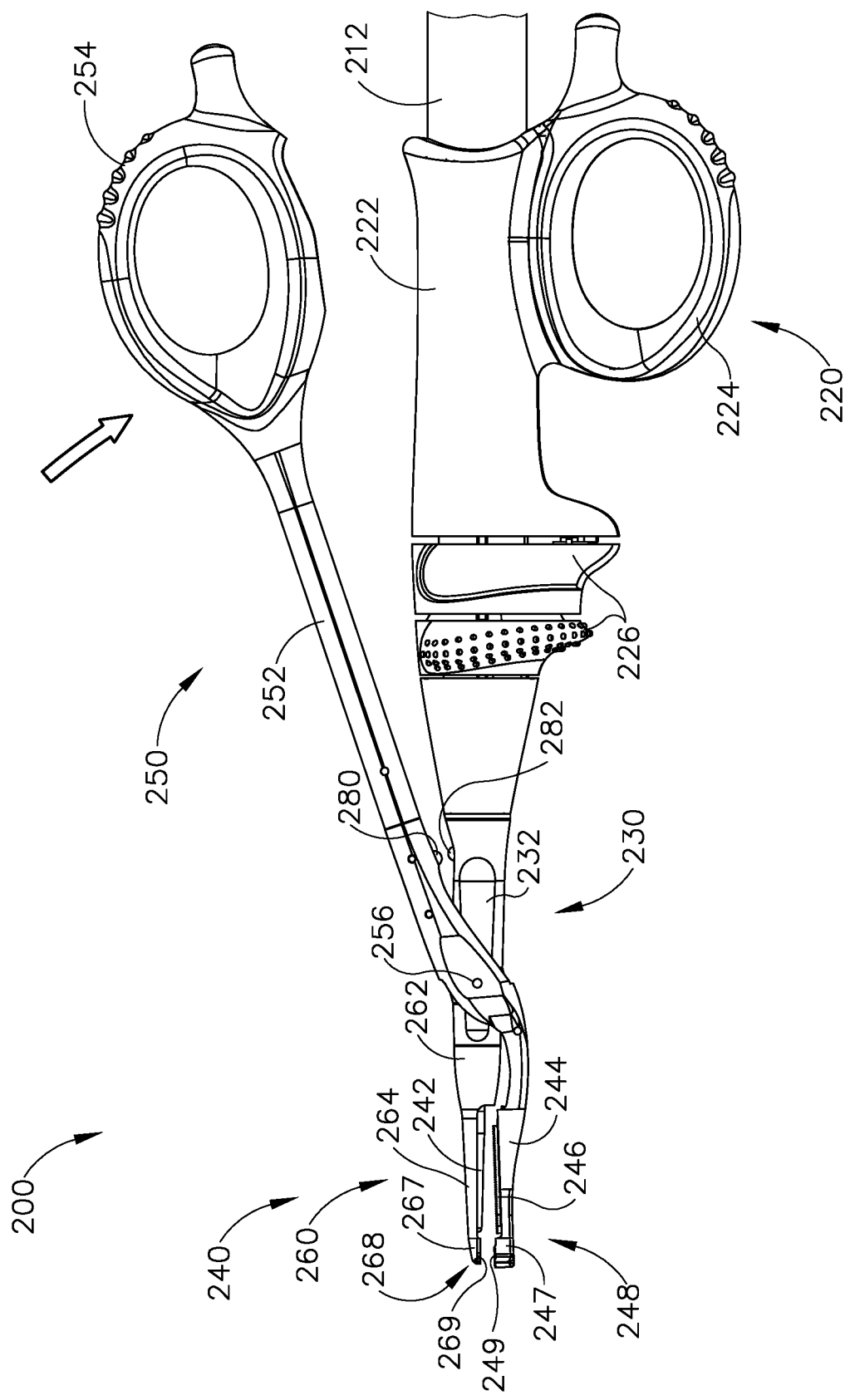
Figure 16C:
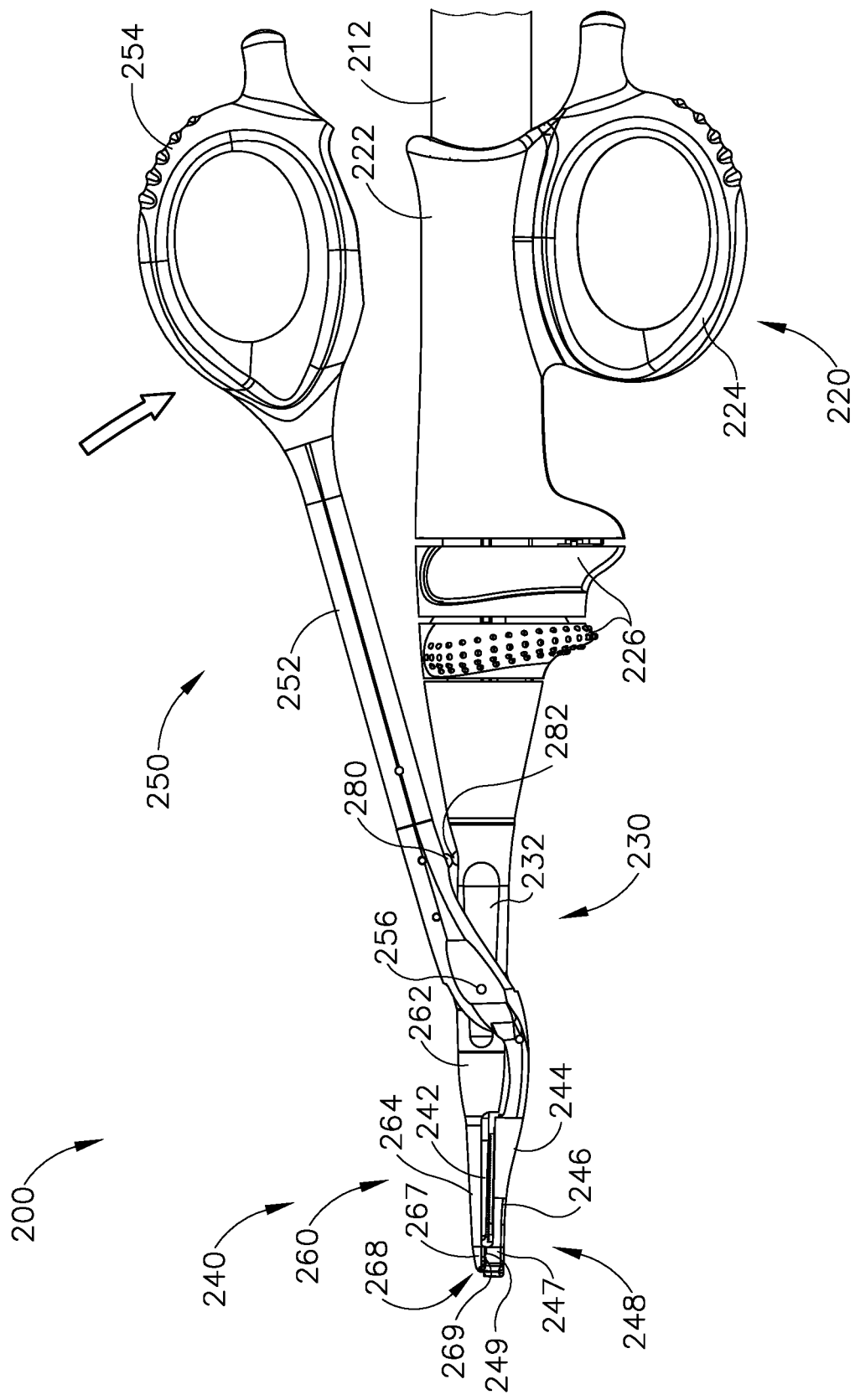
Figure 17:
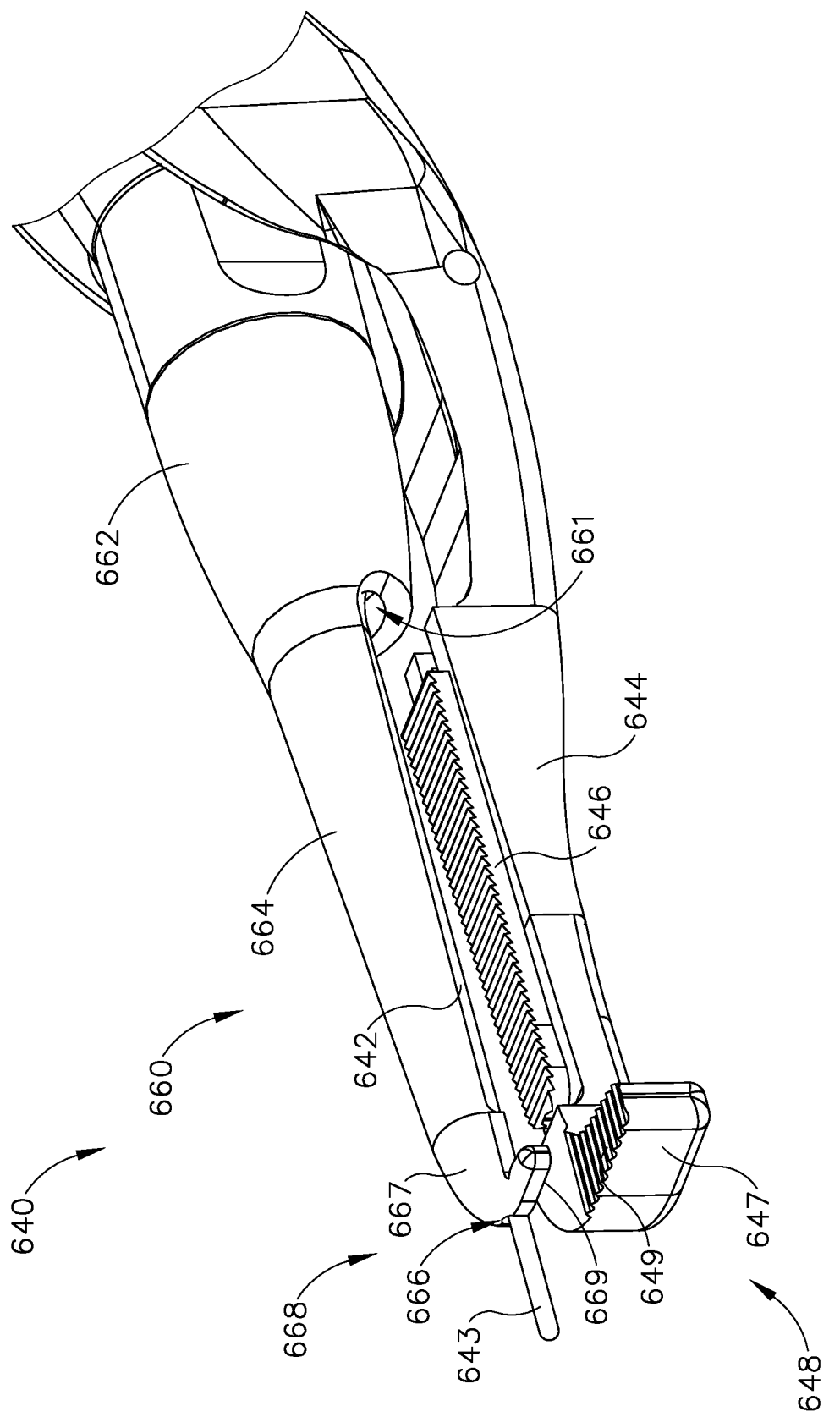
Figure 20:
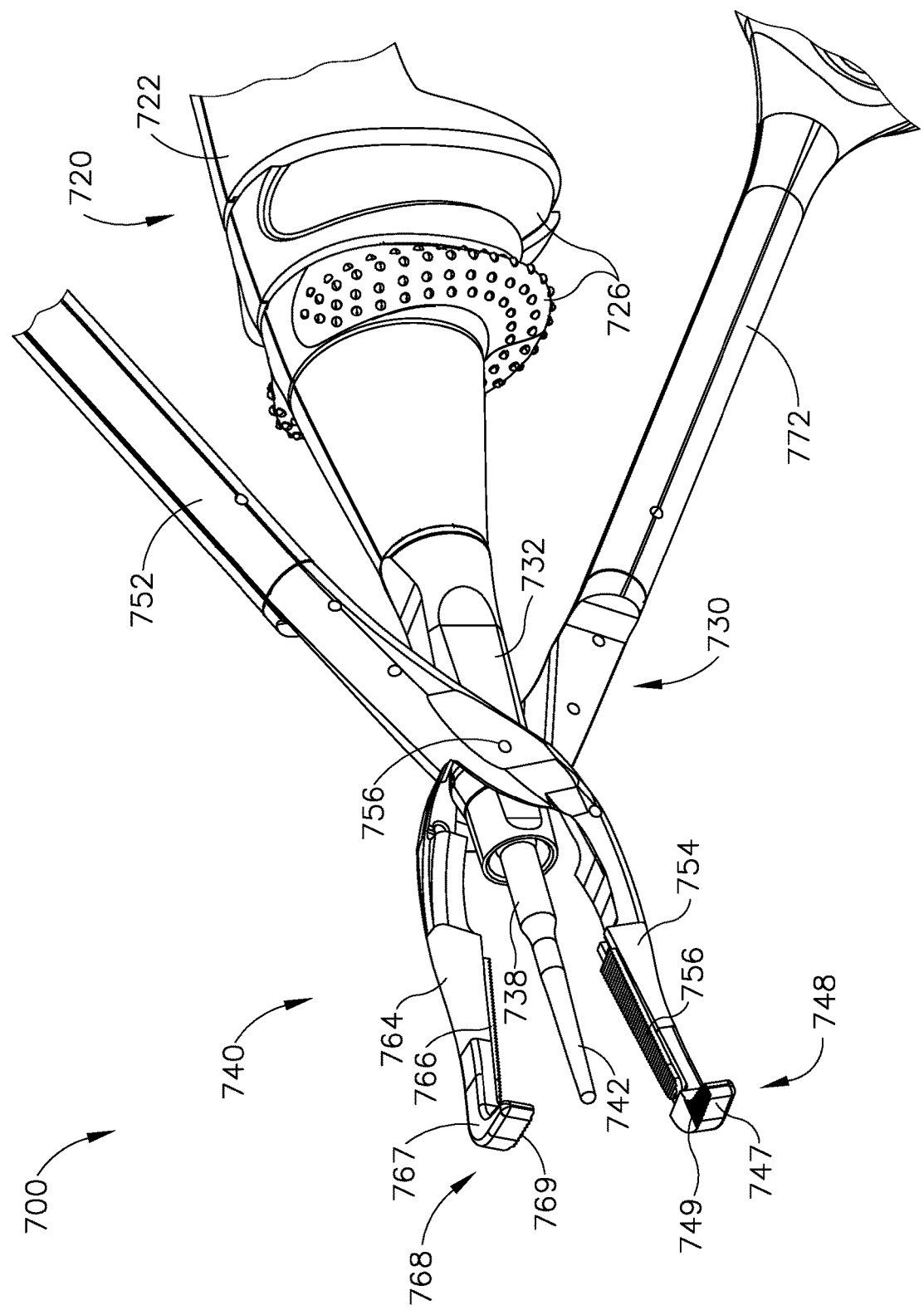
Figure 21A:
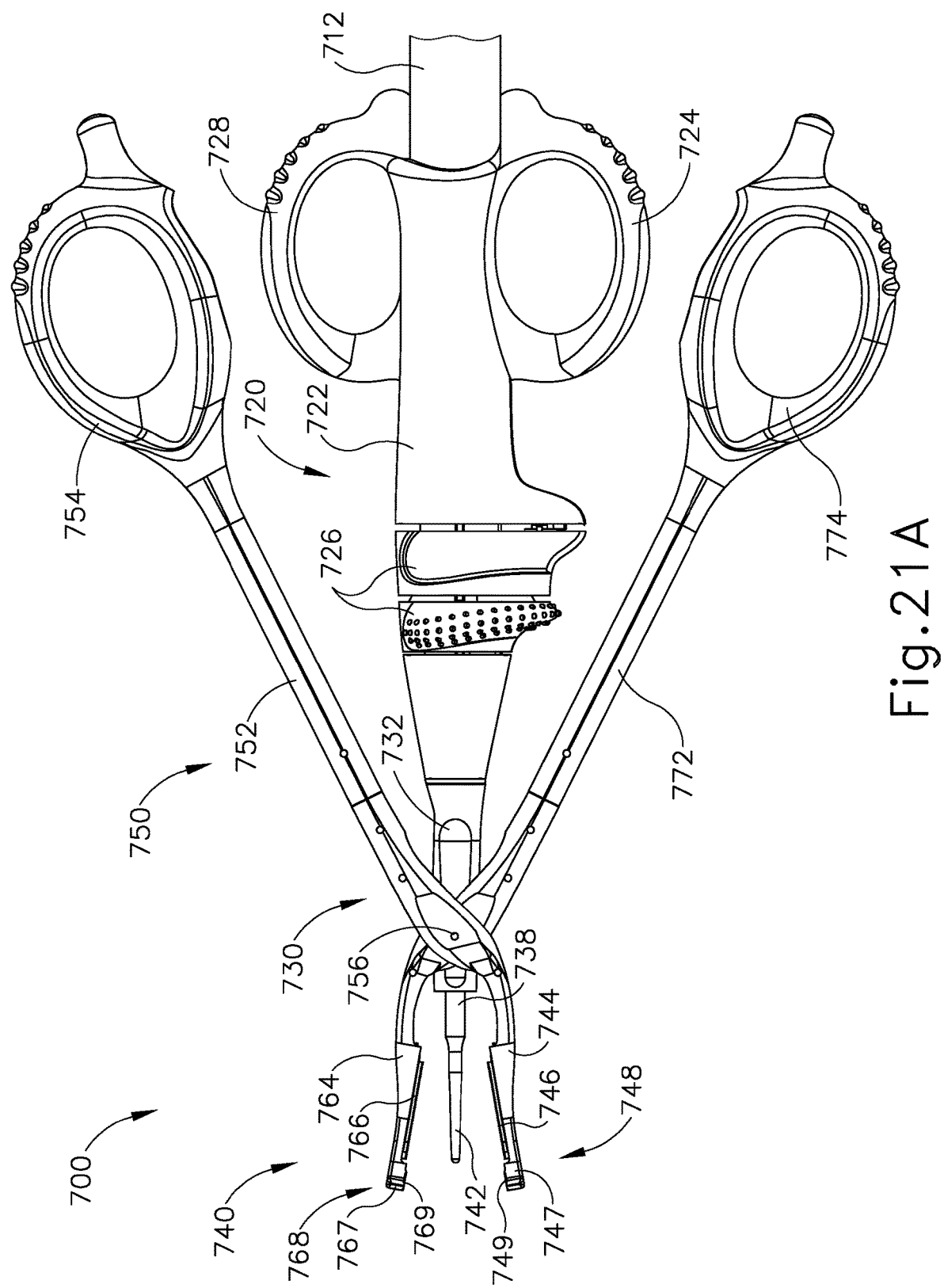
Figure 21B:
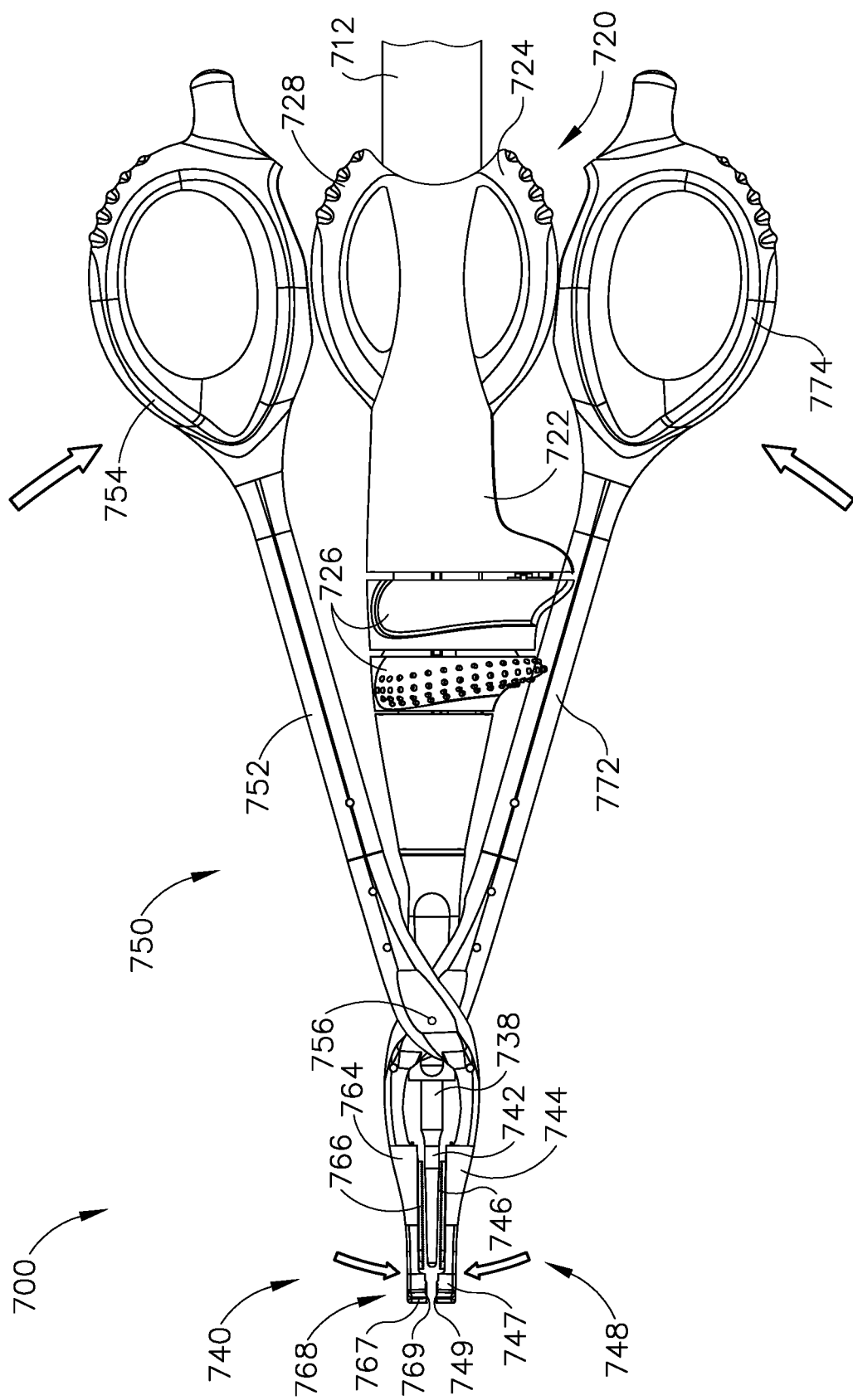

where the end effector is in the first closed configuration as shown in FIG. 12B;

FIG. 13C depicts a cross-sectional rear view of the end effector of FIG. 12A;

where the end effector is in the second closed configuration as shown in FIG. 12C;

FIG. 14A depicts a cross-sectional side view of another alternative end effector that may be readily incorporated into the surgical instrument of FIG. 1, where the end effector is in an open configuration;

FIG. 14B depicts a cross-sectional side view of the end effector of FIG. 14A, where the end effector is in a first closed configuration;

FIG. 14C depicts a cross-sectional side view of the end effector of FIG. 14A, where the end effector is in a second closed configuration;

FIG. 15A depicts a cross-sectional rear view of the end effector of FIG. 14A, where the end effector is in the open configuration as shown in FIG. 14A;

FIG. 15B depicts a cross-sectional rear view of the end effector of FIG. 14A;

where the end effector is in the first closed configuration as shown in FIG. 14B;

FIG. 15C depicts a cross-sectional rear view of the end effector of FIG. 14A;

where the end effector is in the second closed configuration as shown in FIG. 14C;

FIG. 16A depicts a side view of an exemplary alternative surgical instrument with the end effector of FIG. 4, where the end effector is in an open configuration;

FIG. 16B depicts a side view of the surgical instrument of FIG. 16A, where the end effector is in a first closed configuration;

FIG. 16C depicts a side view of the surgical instrument of FIG. 16A, where the end effector is in a second closed configuration;

FIG. 17 depicts a perspective view of another alternative end effector that may be readily incorporated into the surgical instruments of FIG. 1 or FIG. 16A, where the end effector is in a closed configuration;

FIG. 18 depicts a top plan view of the end effector of FIG. 17;

FIG. 19 depicts a bottom plan view of a selected portion of the end effector of FIG. 17;

FIG. 20 depicts a perspective view of an exemplary alternative surgical instrument, where the surgical instrument is in an open configuration;

FIG. 21A depicts a side elevational view of the surgical instrument of FIG. 20, where the surgical instrument is in the open configuration as shown in FIG. 20; and FIG. 21B depicts a side elevational view of the surgical instrument of FIG. 20, where the surgical instrument is in a closed configuration.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument for Open Surgical Procedures

FIG. 1 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 2:
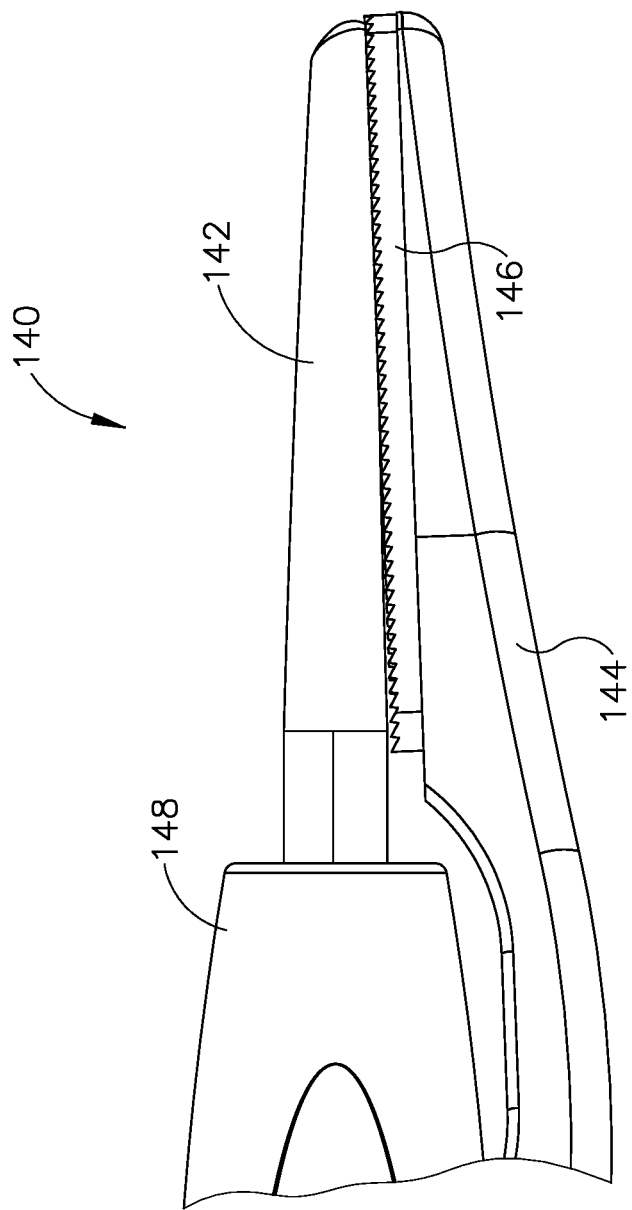
FIG. 2 depicts a side elevational view of the end effector of the instrument of FIG. 1, in a closed configuration.
Figure 3A:
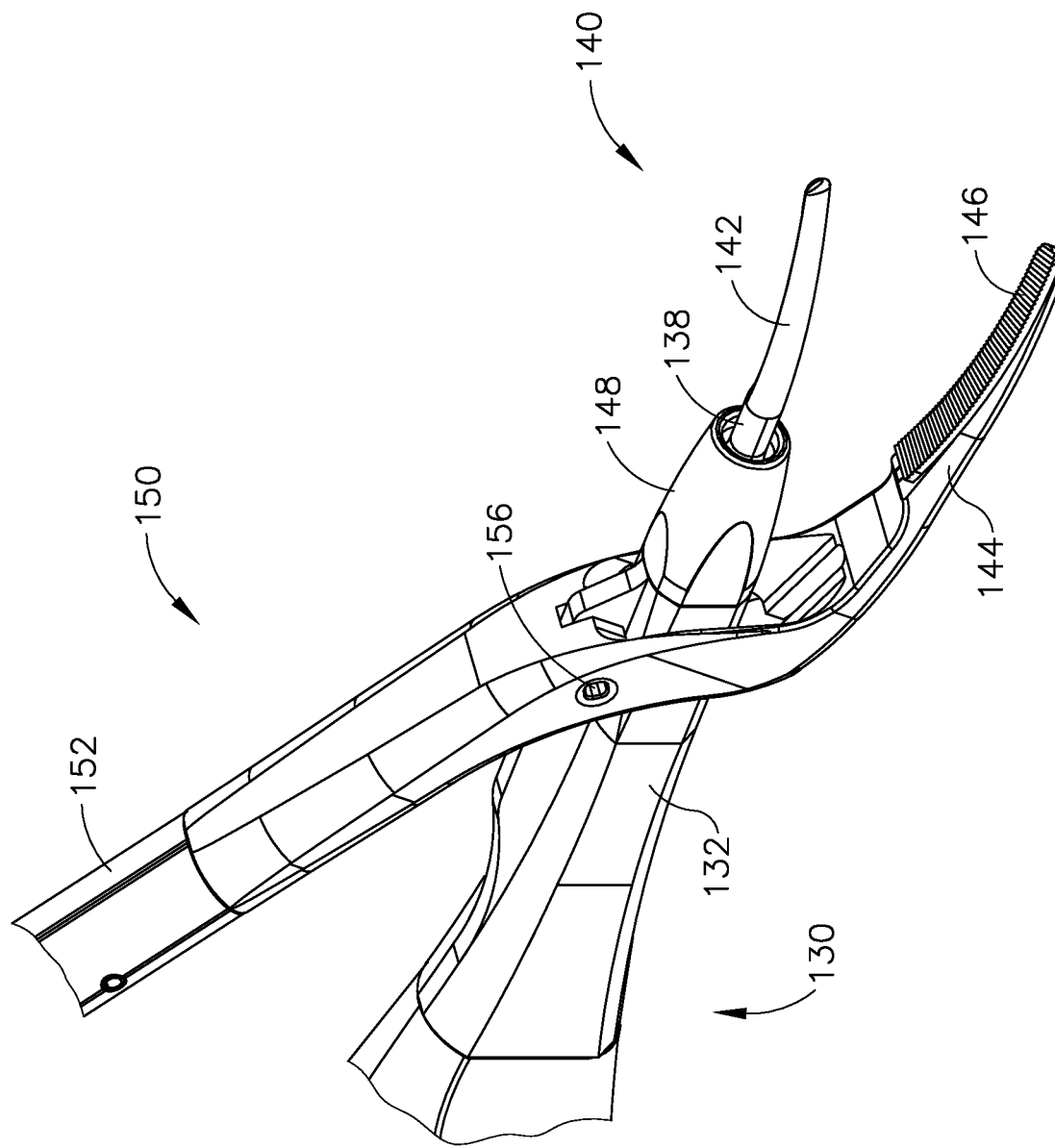
FIG. 3A depicts a perspective view of the end effector of FIG. 2, in an open configuration.
Figure 3B:
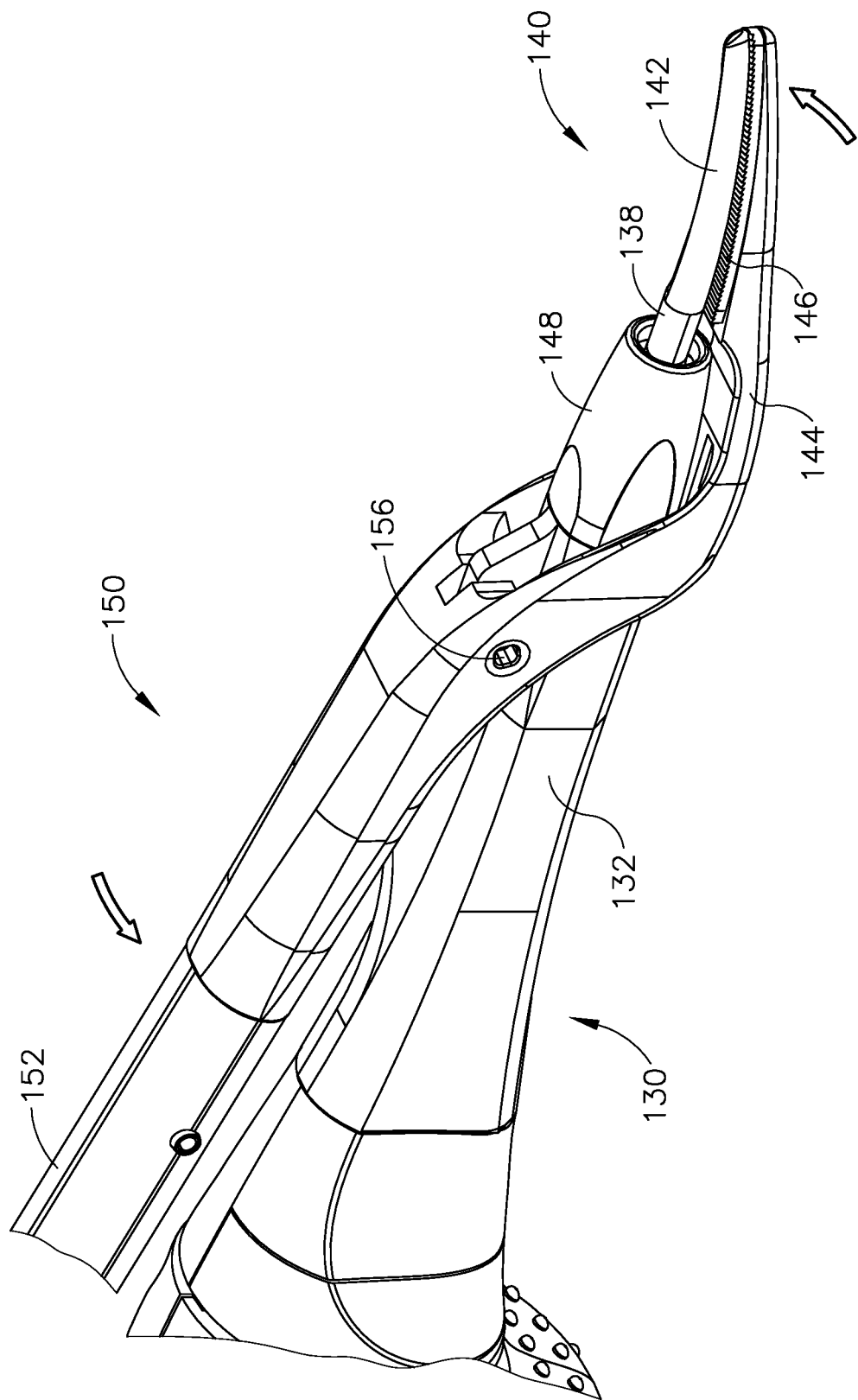
FIG. 3B depicts a perspective view of the end effector of FIG. 2, in a closed configuration.

Shaft assembly (130) comprises an outer sheath (132) extending distally from body (122). As best seen in FIGS. 2-3B, end effector (140) comprises an ultrasonic blade (142), a clamp arm (144), and a cap (148) secured to the distal end of sheath (132). Ultrasonic blade (142) extends distally from cap (148). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 3A-3B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open configuration shown in FIG. 3A. By way of example only, such a resilient member may comprise a leaf spring, a torsion spring, and/or any other suitable kind of resilient member.

Referring back to FIG. 1, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric or magnetorestrictive principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (142), thereby providing oscillation of ultrasonic blade (142) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713 now abandoned; U.S. Pub. No. 2007/0282333, now abandoned; U.S. Pub. No. 2008/0200940₁ now abandoned; U.S. Pub. No. 2010/0069940, issued as U.S. Pat. No. 9,023,071 on May 5, 2015; U.S. Pub. No. 2011/0015660, issued as U.S. Pat. No. 8,461, 744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2014/0114334, issued as U.S. Pat. No. 9,095,367 on Aug. 4, 2015; and/or U.S. patent application Ser. No. 14/031,665 now abandoned. Additional merely illustrative variations for instrument (100) will be described in greater detail below. It should be understood that the below described variations may be readily applied to instrument (100) described above and any of the instruments referred to in any of the references that are cited herein, among others.

II. Exemplary End Effectors with Passive Dissection Features

In some instances, it may be desirable to grasp and/or manipulate tissue via end effector (140) without ultrasonic blade (142) contacting tissue. For example, during operation, ultrasonic blade (142) may build up excess thermal energy. Passively grasping tissue via end effector (140) may lead to contact between tissue and ultrasonic blade (142). If prior activation of ultrasonic blade (142) leads to a buildup of excess thermal energy, contact between ultrasonic blade (142) and tissue may lead to undesired effects, such as burning of tissue. Additionally, an operator may desire to simply grasp tissue or perform a blunt dissection on tissue without transmitting mechanical oscillations through ultrasonic blade (142). For example, an operator may desire to grasp tissue with end effector (140) in order to effectively pinch and/or crush tissue between end effector (140), thereby severing grasped tissue. An operator may also desire to insert end effector (140), in a closed configuration, between two organs or anatomical parts that are attached and/or stuck together. The operator may then open end effector (140) to an open configuration in order to pry apart or separate attached organs or anatomical parts.

It should be understood from the foregoing that may be advantageous to configure end effector (140) in a way that facilitates use of end effector (140) to perform simple grasping or blunt dissection tasks, without necessarily having the tissue contact blade (142). The following description provides various examples of how end effector (140) may be reconfigured to facilitate simple grasping or blunt dissection tasks. Other variations will be apparent to those of ordinary skill in the art in view of the teachings herein.

A. End Effector with Distal, Laterally Extending Tines

FIGS. 4-9 show an end effector (240) that may be readily incorporated into ultrasonic surgical instrument (100) described above. End effector (240) comprises an ultrasonic blade (242), a clamp arm (244), and a blade guard (260) secured to the distal end of sheath (132). Ultrasonic blade (242) is integrally connected to a waveguide (238). Ultrasonic blade (242) and waveguide (238) are substantially similar to ultrasonic blade (142) and waveguide (138) described above. Therefore, waveguide (238) may communicate ultrasonic vibrations to ultrasonic blade (242).

Clamp arm (244) includes a clamp pad (246) facing ultrasonic blade (142). Clamp arm (244) is substantially similar to clamp arm (144) described above, while clamp pad (246) is substantially similar to clamp pad (146) described above, with differences described below. Therefore, clamp arm (244) is an integral feature of clamp arm assembly (150). Additionally, clamp arm (244) is pivotable toward and away from ultrasonic blade (242) based on pivoting of thumb grip ring (154) toward and away from body (133) of handle assembly (120).

A clamp tine (248) is positioned at the distal end of clamp arm (244). Clamp tine (248) comprises a laterally extending body (247) and a grasping surface (249). Laterally extending body (247) projects laterally away from the longitudinal axis defined by ultrasonic blade (242), although this is merely optional. The offset position of laterally extending body (247) relative to the longitudinal axis defined by ultrasonic blade (242) may allow an operator to better visualize clamp tine (248) during use of end effector (240). Grasping surface (249) provides a plurality of ridges in this example, however it should be understood that ridges are merely optional. For instance, grasping surface (249) may comprise a flat surface, an inclined surface, a waved surface, a knurled surface, or have any other suitable geometry as would be apparent to one having ordinary skill in the art in view of the teachings herein. As will be described in greater detail bellow, clamp tine (248) is configured to rotate with clamp arm (244) toward and away from blade guard (260) to passively grasp and/or perform blunt dissections on tissue.

Figure 9:
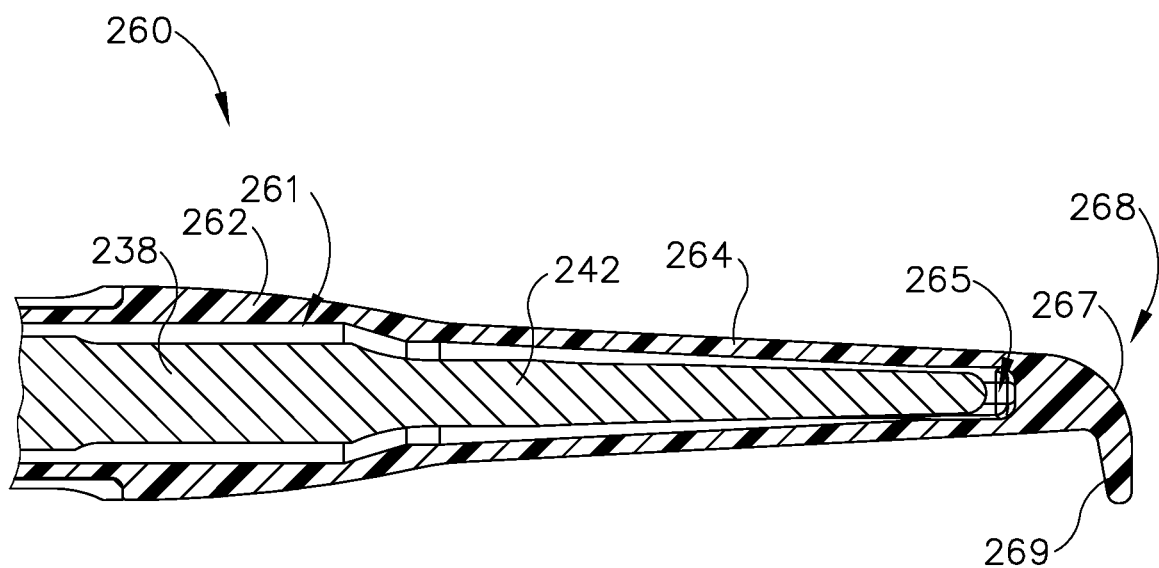
FIG. 9 depicts a cross-sectional bottom view of a selected portion of the end effector of FIG. 4.

Blade guard (260) comprises a cap (262), a longitudinally extending arm (264), and a guard tine (268). Cap (262) is secured to the distal end of sheath (132). Additionally, cap (262) defines a tubular passage (261), which waveguide (238) extends through. As best seen in FIG. 9, tubular passage (261) is sized to accommodate the outer diameter of waveguide (238) such that waveguide (238) does not contact the inner surface of cap (262) when waveguide (238) mechanically oscillates.

Longitudinally extending arm (264) unitarily extends from cap (262) along the length of ultrasonic blade (242). As best shown in FIGS. 6A-9, longitudinally extending arm (264) defines a hollow or concave pathway (265) that houses a portion of ultrasonic blade (242). In particular, longitudinally extending arm (264) may house ultrasonic blade (242) so that the portion of ultrasonic blade (242) facing toward clamp pad (266) is exposed while the portion of ultrasonic blade (242) facing away from clamp pad (266) is confined within longitudinally extending arm (264). As will be described in greater detail below, longitudinally extending arm (264) may act as a heat guard for ultrasonic blade (242).

Concave pathway (265) of longitudinally extending arm (264) is dimensioned to form a gap between the outer diameter of ultrasonic blade (242) and the inner surface of longitudinally extending arm (264) defining concave pathway (265). The gap formed by concave pathway (265) is large enough so that ultrasonic blade (242) does not contact the inner surface of longitudinally extending arm (264) when ultrasonic blade (242) mechanically oscillates. This may prevent unwanted contact between ultrasonic blade (242) and blade guard (260).

Guard tine (268) is positioned at the distal end of longitudinally extending arm (264). Guard tine (268) comprises a laterally extending body (267) and a grasping surface (269). Laterally extending body (267) projects laterally away from the longitudinal axis defined by ultrasonic blade (242), although this is merely optional. The offset position of laterally extending body (267) relative to the longitudinal axis defined by ultrasonic blade (242) may allow an operator to better visualize guard tine (268) during use of end effector (240). Grasping surface (269) of guard tine (268) forms a flat surface facing toward grasping surface (249) of clamp tine (248). While in the current example, grasping surface (269) forms a flat surface, this is merely optional. For instance, grasping surface (269) may include a plurality of ridges, an include surface, a waved surface, a knurled surface, or have any other suitable geometry as would be apparent to one having ordinary skill in the art in view of the teachings herein.

It should be understood that laterally extending body (267) of guard tine (268) extends in the same general direction of laterally extending body (247) of clamp tine (248). While the current example shows laterally extending bodies (267, 247) extending in a linear fashion, laterally extending body (267) of guard tine (268) and laterally extending body (247) of clamp tine (248) may extend to form a curve while in the closed position. For instance, laterally extending bodies (267, 247) may curve upwardly and away from the plane defined by the clamping surface of clamp pad (246). Additionally, while the current example shows laterally extending bodies (267, 247) extending perpendicularly relative to blade (242), any other suitable angle may be used as would be apparent to one having ordinary skill in the art in view of the teachings herein. For example, blade (242) could have a curved profile while clamp tine (248) and guard tine (268) extend past blade (242) along the same curved profile.

Grasping surface (269) of guard tine (268) and grasping surface (249) of clamp tine (248) at least partially align in both longitudinal and lateral directions while end effector (240) is in a closed configuration. In other words, grasping surfaces (249, 269) are positioned so that rotation of clamp arm (244) toward ultrasonic blade (242) will cause contact between grasping surfaces (249, 269); or at least provide a sufficient distance between grasping surfaces (249, 169) to enable grasping and/or manipulation of tissue between grasping surfaces (249, 269). Although the current figures show clamp tine (248) extending beyond guard tine (268), guard tine (268) may be dimensioned equal to or greater than the dimensions of clamp tine (248). As will be described in greater detail below, this may allow for grasping surfaces (249, 269) to interact with each other in order to passively grasp or passively sever tissue captured between grasping surfaces (249, 269) when clamp arm (244) rotates toward ultrasonic blade (242).

Figure 5A:
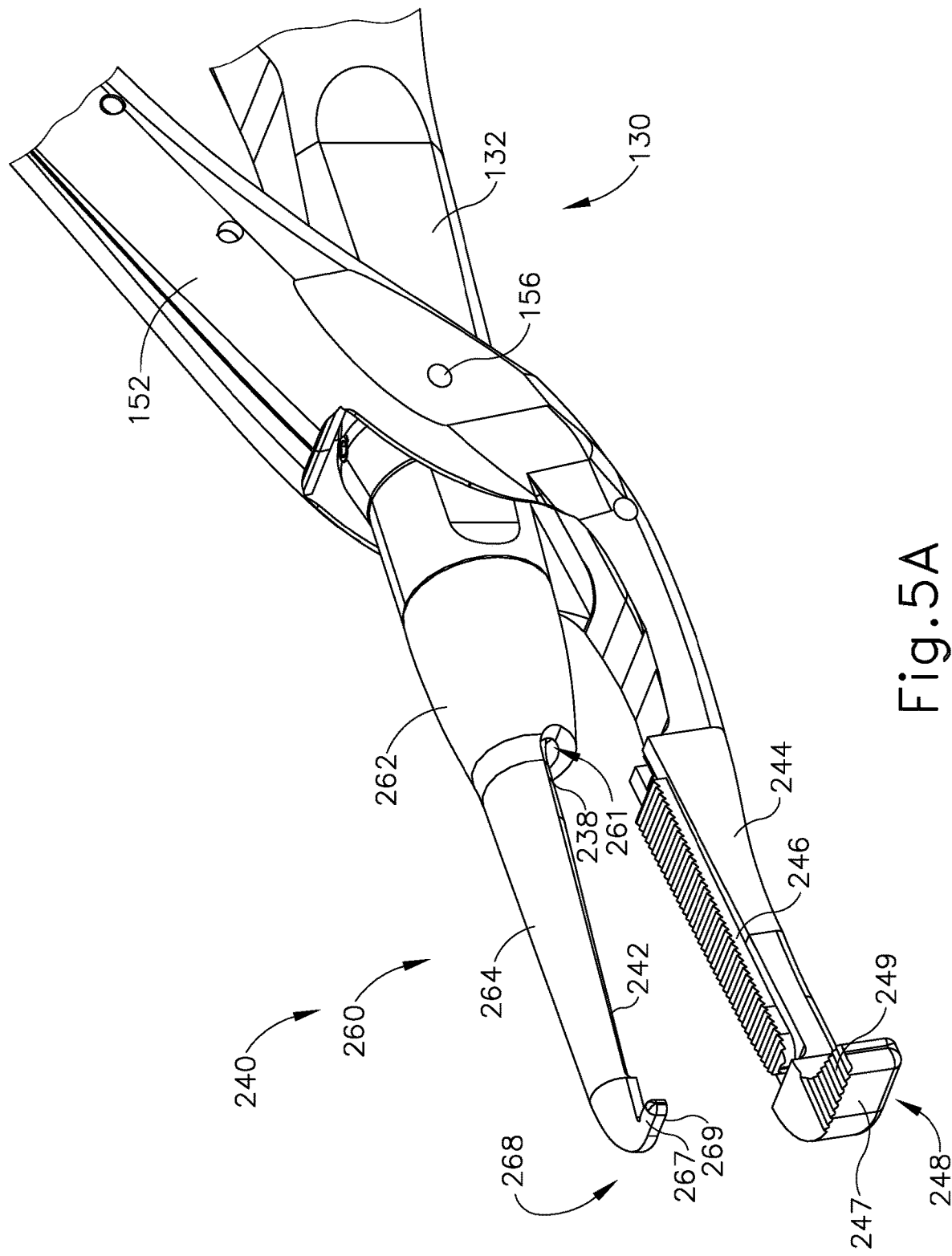
FIG. 5A depicts a perspective view of the end effector of FIG. 4, in an open configuration.
Figure 5B:
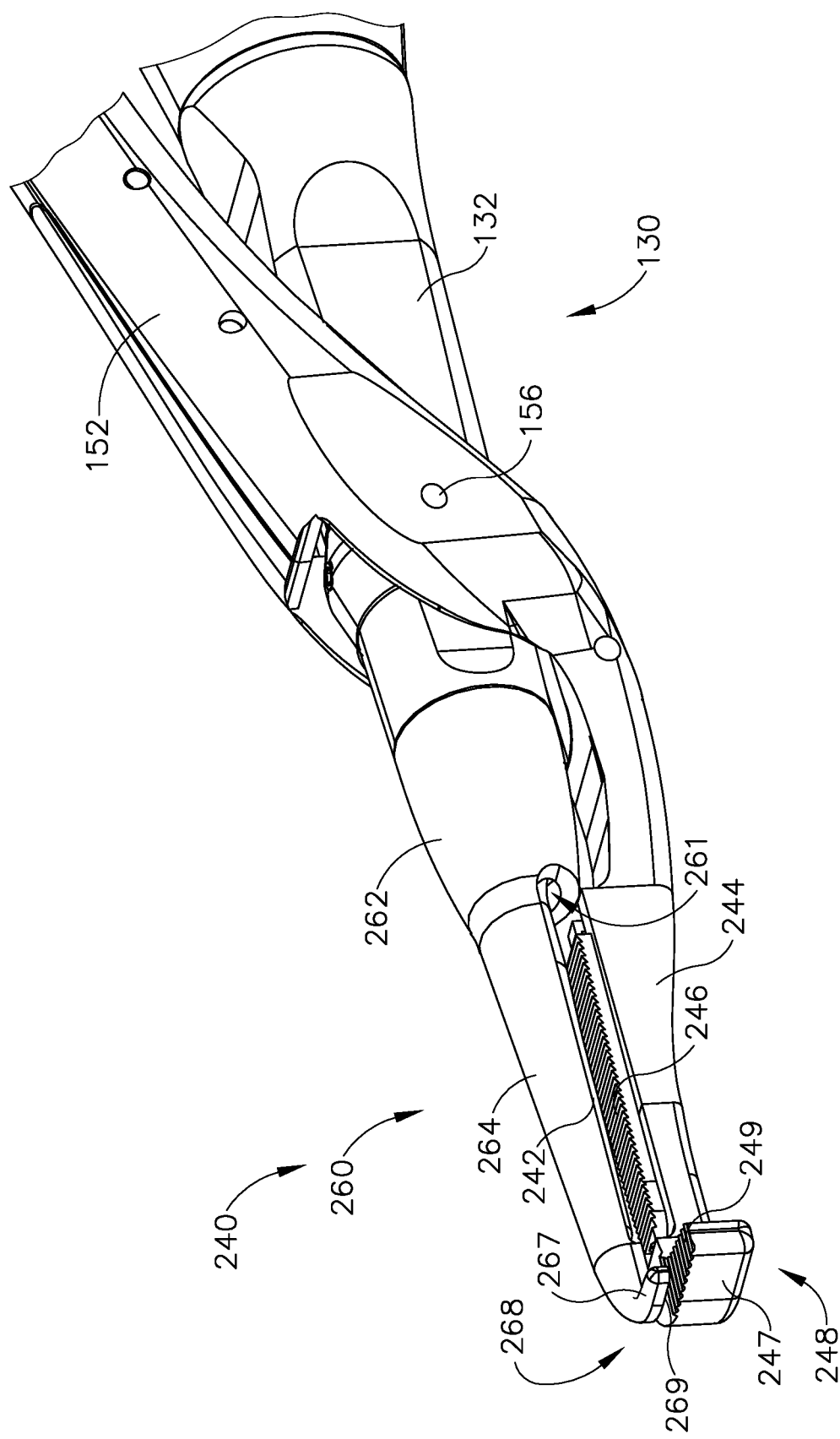
FIG. 5B depicts a perspective view of the end effector of FIG. 4, in a closed configuration.
Figure 6B:
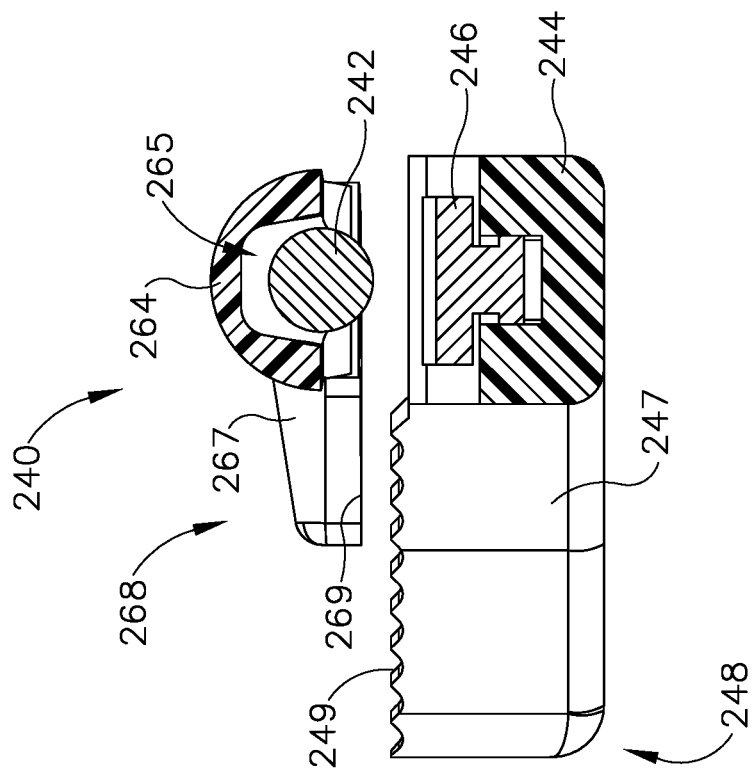
FIG. 6B depicts a cross-sectional rear view of the end effector of FIG. 4, in the closed configuration as shown in FIG. 5B.

FIGS. 5A-6B show end effector (240) transition from an open configuration (FIGS. 5A and 6A) to a closed configuration (FIGS. 5B and 6B). In exemplary use, an operator may rotate clamp arm (244) toward ultrasonic blade (242) so that grasping surfaces (249, 269) align to grasp tissue. The operator may either move instrument (100) in order to move grasped tissue or further rotate tines (248, 268) together in order to form a blunt dissection. Additionally or alternatively, the operator may rotate clamp arm (244) so that tissue is captured between clamp pad (246) and ultrasonic blade (242), then activate ultrasonic blade (242) in order to cut through and seal tissue. Therefore, an operator may choose between either performing a blunt dissection (or simple grasping of tissue), or operating on tissue with an active ultrasonic blade (242), with one single end effector (240) being capable of performing all of these kinds of tasks. While in the current example, tines (248, 268) are used to grasp tissue and/or form a blunt dissection, tines (248, 268) may also be dimensioned and manipulated to perform fine dissection of tissue.

Figure 6A:
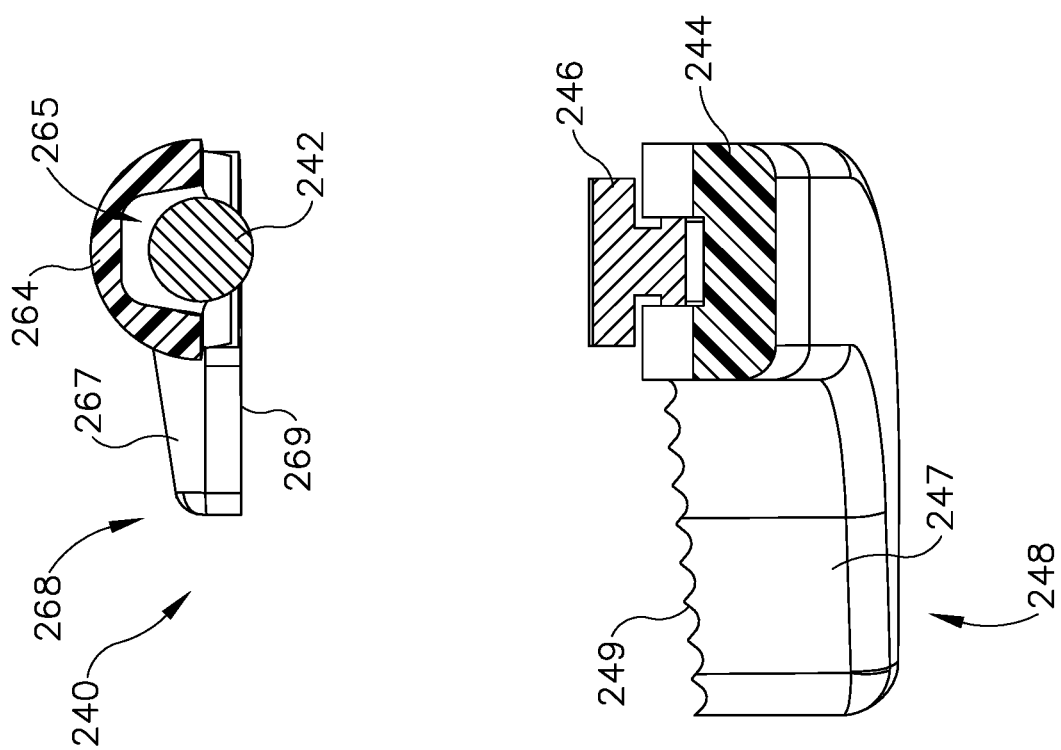
FIG. 6A depicts a cross-sectional rear view of the end effector of FIG. 4, in the open configuration as shown in FIG. 5A.
Figure 7:
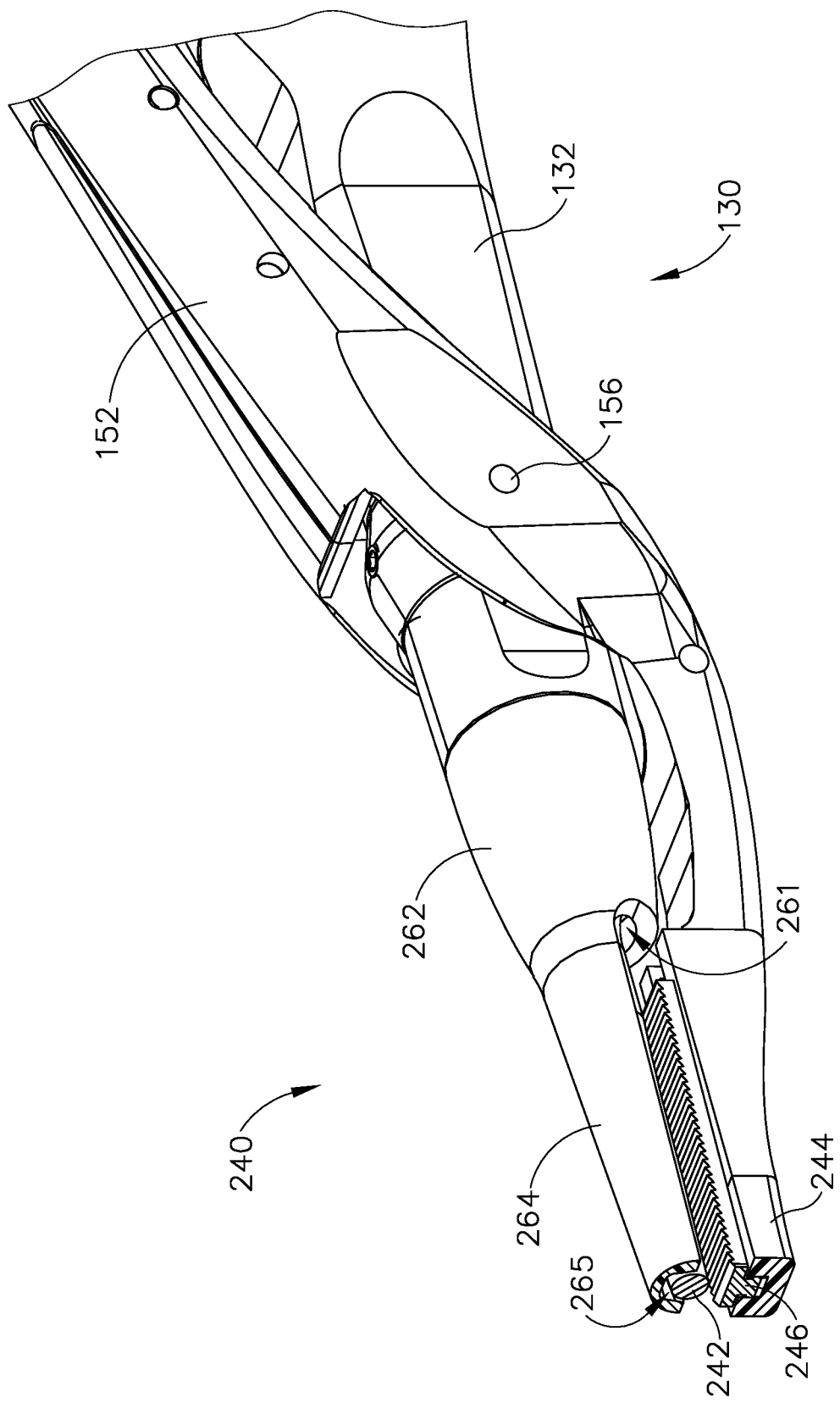
FIG. 7 depicts a cross-sectional perspective view of the end effector of FIG. 4.
Figure 8:
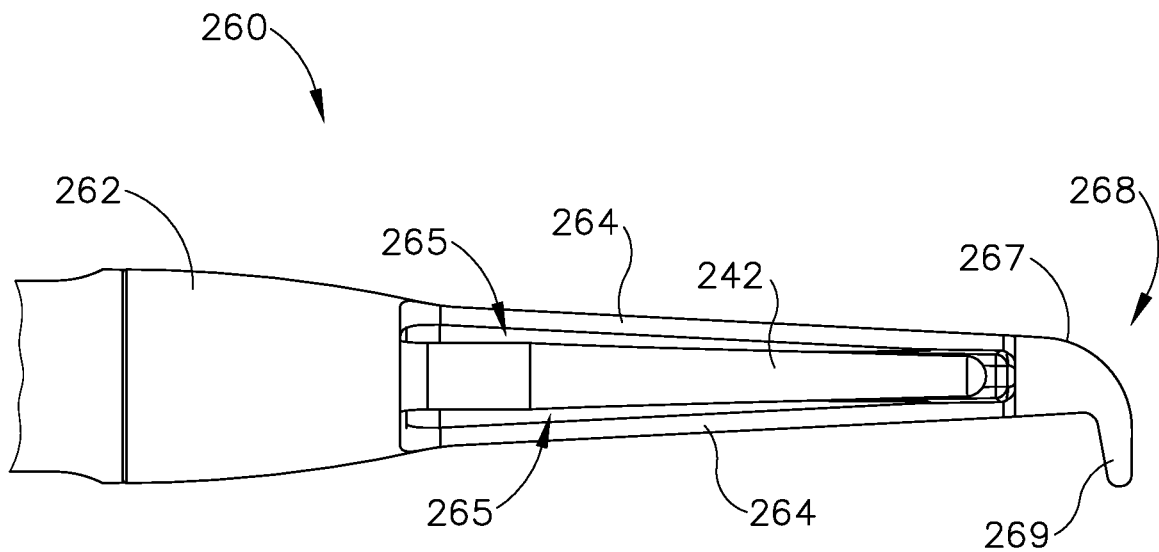
FIG. 8 depicts a bottom plan view of a selected portion of the end effector of FIG. 4.

Additionally, an operator may manipulate tissue by transitioning end effector (240) from a closed configuration (FIGS. 5B and 6B) to an open configuration (FIGS. 5A and 6A). For instance, the operator may insert end effector (240) in a closed configuration between two organs or anatomical parts that are attached and/or stuck together. Once end effector (240) is placed in the desired location, the operator may open end effector (240) to separate the two organs or anatomical parts without exposing ultrasonic blade (242) to the targeted structures. In other words, clamp arm (244) and blade guard (260) may sufficiently shield ultrasonic blade (242) from tissue while end effector (240) is in a closed configuration such that end effector (240) may be inserted between two organs or anatomical parts in a closed configuration without imparting undesired heat to the tissue. Subsequently, end effector (240) may transition to an opened configuration so that the outer surface of blade guard (260) and the outer surface of clamp arm (244) make contact with the desired anatomical structure and separate the tissue layers without unwanted contact between the tissue and ultrasonic blade (242).

B. End Effector with Two Stage Closure and Resilient Tines

Figure 10A:
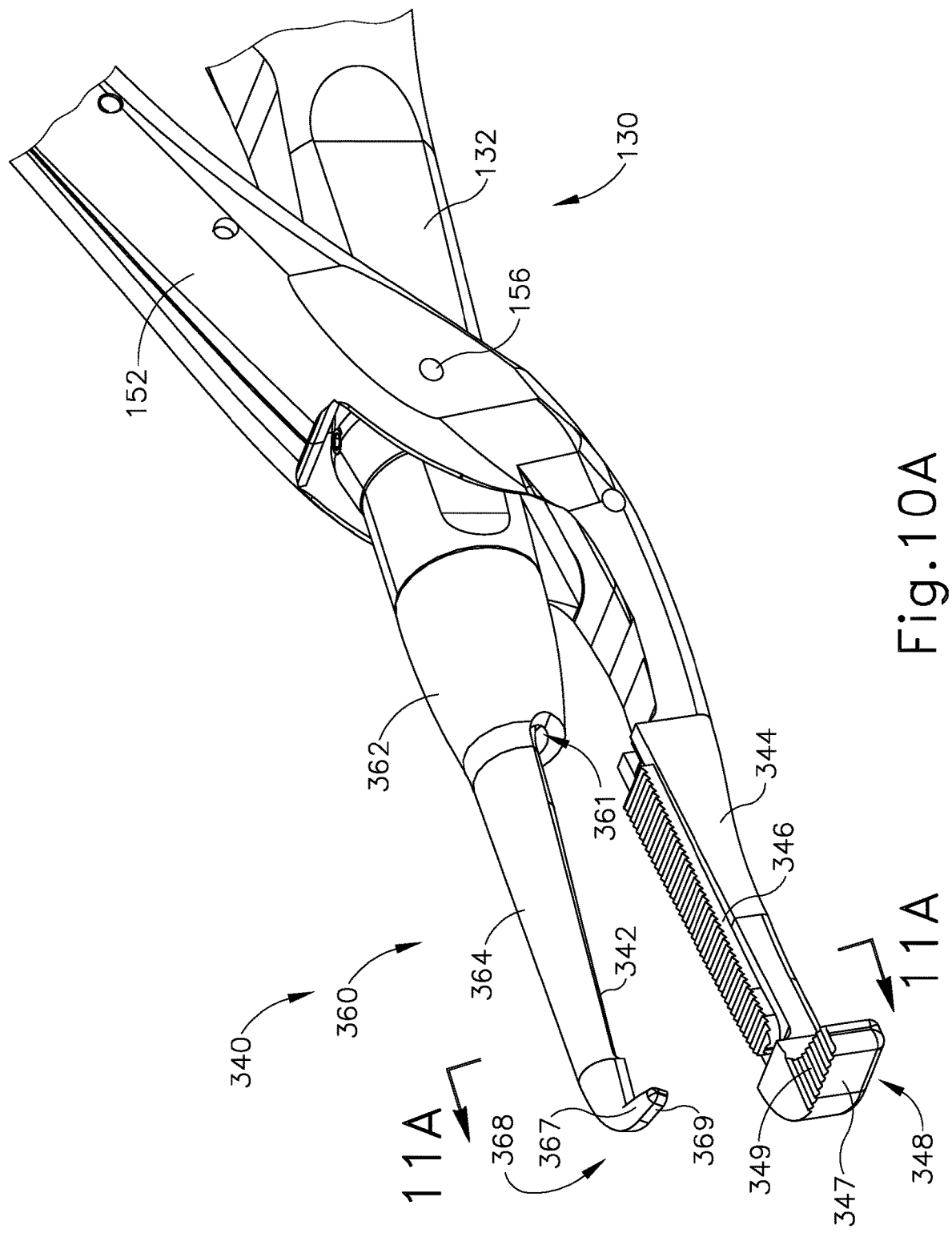
FIG. 10A depicts a perspective view of another alternative end effector that may be readily incorporated into the surgical instrument of FIG. 1, where the end effector is in an open configuration
Figure 10B:
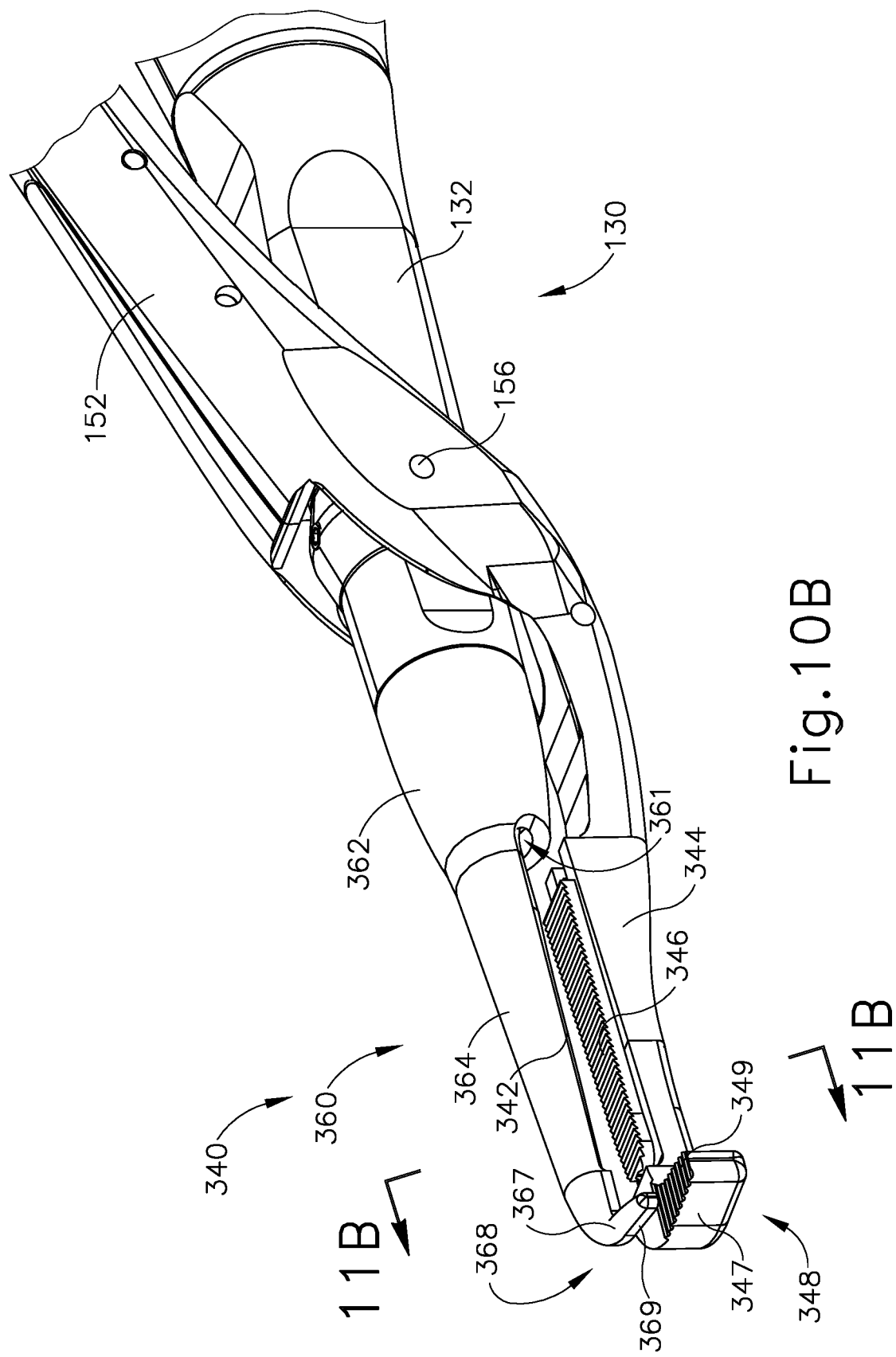
FIG. 10B depicts a perspective view of the end effector of FIG. 10A, where the end effector is in a first closed configuration.
Figure 10C:
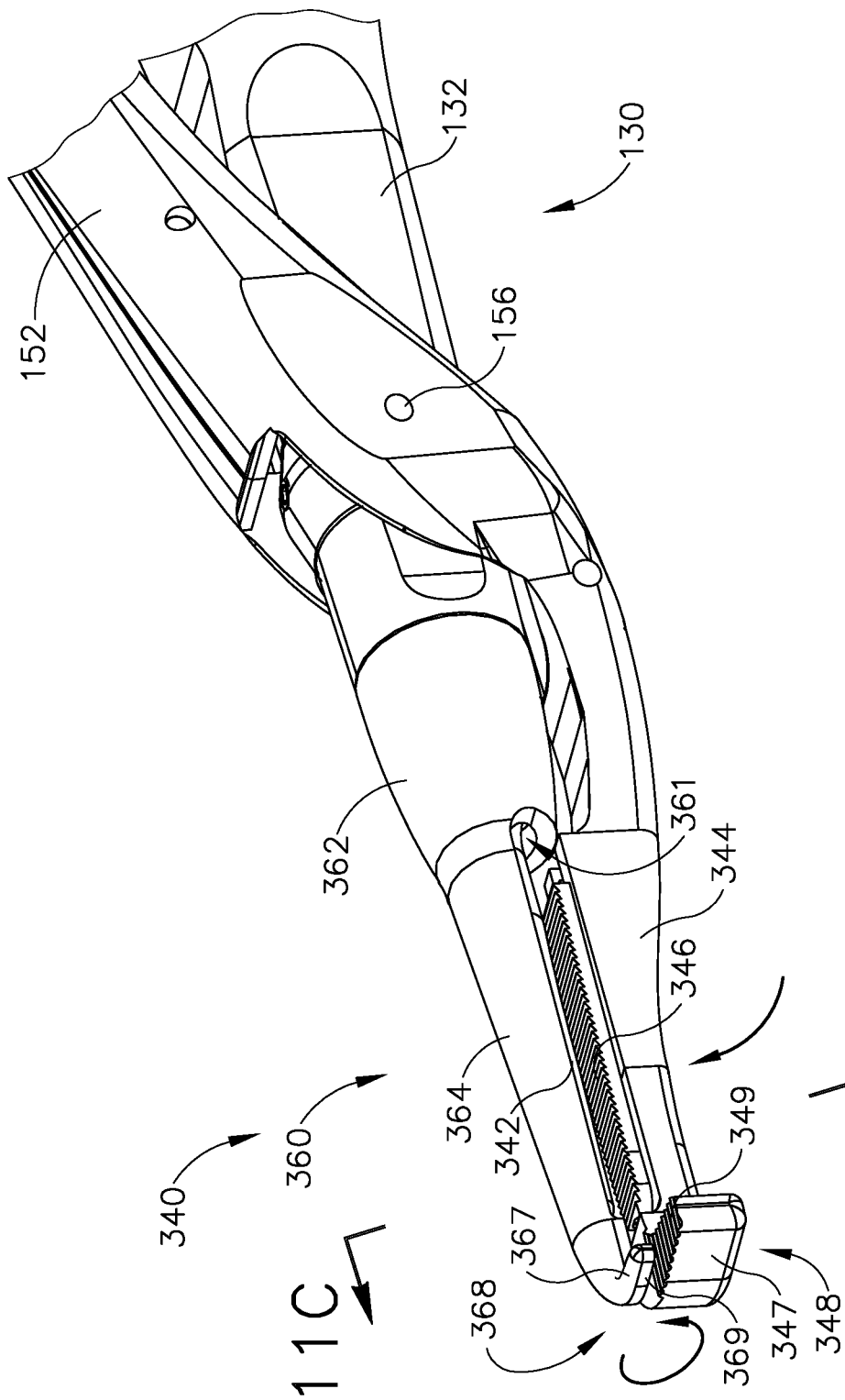
FIG. 10C depicts a perspective view of the end effector of FIG. 10A, where the end effector is in a second closed configuration.
Figure 11C:
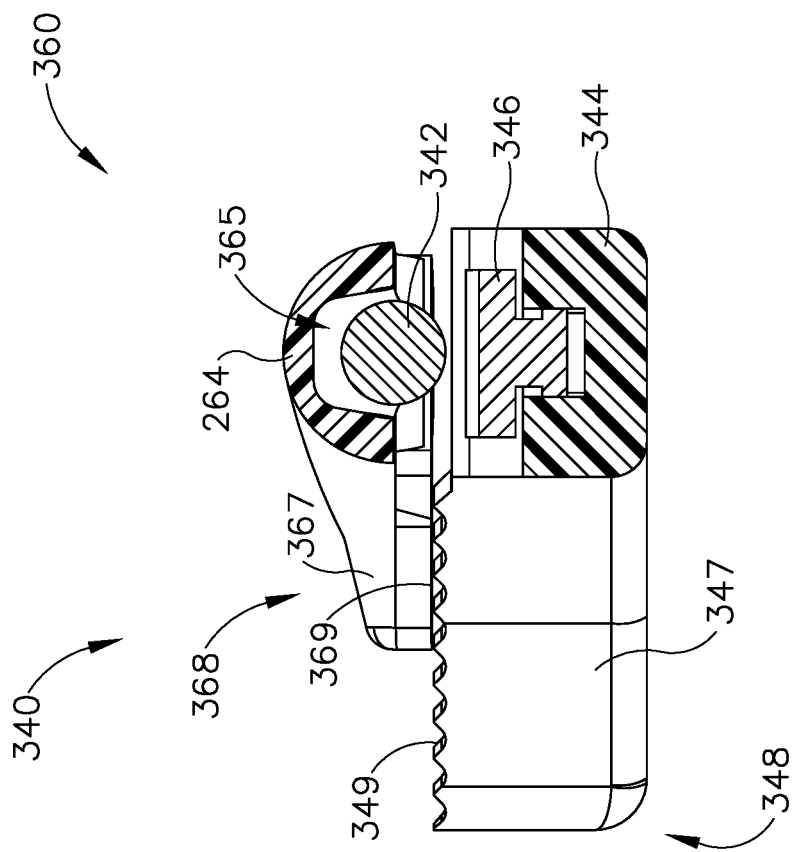
FIG. 11C depicts a cross-sectional rear view of the end effector of FIG. 10A, taken along line 11C-11C—of FIG. 10C, where the end effector is in the second closed configuration as shown in FIG. 10C.

FIGS. 10A-11C show another alternative end effector (340) that may be readily incorporated into ultrasonic surgical instrument (100) described above. While end effector (240) is configured to transition from an open configuration to a closed configuration, as shown in FIGS. 5A-6B, end effector (340) is configured to transition from an open configuration, as shown in FIGS. 10A and 11A, to a first closed configuration, as shown in FIGS. 10B and 11B, and finally to a second closed configuration, as shown in FIGS. 10C and 11C. As will be described in greater detail below, the first closed configuration may allow an operator to passively grasp and/or manipulate desired tissue while the second closed configuration may allow an operator to capture tissue between an ultrasonic blade and a clamp pad with sufficient force required to cut through and seal tissue with an activated ultrasonic blade.

End effector (340) of this example comprises an ultrasonic blade (342), a clamp arm (344), and a blade guard (360) secured to the distal end of sheath (132). Ultrasonic blade (342) is integrally connected to a waveguide (338). Ultrasonic blade (342) and waveguide (338) are substantially similar to ultrasonic blade (142, 242) and waveguide (138, 238) described above. Therefore, waveguide (338) may communicate ultrasonic vibrations to ultrasonic blade (342).

Clamp arm (344) includes a clamp pad (346) facing ultrasonic blade (342). Clamp arm (344) is substantially similar to clamp arm (244) described above, while clamp pad (346) is substantially similar to clamp pad (246) described above, with differences described below. Therefore, clamp arm (344) is an integral feature of clamp arm assembly (150). Additionally, clamp arm (344) is pivotable toward and away from ultrasonic blade (342) based on pivoting of thumb grip ring (154) toward and away from body (133) of handle assembly (120).

A clamp tine (348) is positioned at the distal end of clamp arm (344). Clamp tine (348) comprises a laterally extending body (347) and a grasping surface (349). Laterally extending body (347) projects laterally away from the longitudinal axis defined by ultrasonic blade (342), although this is merely optional. The offset position of laterally extending body (347) relative to the longitudinal axis defined by ultrasonic blade (342) may allow an operator to better visualize clamp tine (348) during use of end effector (340). Grasping surface (349) of this example has a plurality of ridges, however it should be understood that ridges are merely optional. For instance, grasping surface (349) may have a flat surface, an inclined surface, a waved surface, a knurled surface or have any other suitable geometry as would be apparent to one having ordinary skill in the art in view of the teachings herein. As will be described in greater detail bellow, clamp tine (348) is configured to rotate with clamp arm (344) toward and away from blade guard (360) to passively grasp and/or perform blunt dissections on targeted tissue.

Blade guard (360) comprises a cap (362), a longitudinally extending arm (364) and a resiliently flexible guard tine (368). Cap (362) is substantially similar to cap (262) as described above. Therefore, cap (362) is secured to the distal end of sheath (132). Additionally, cap (362) defines a tubular passage (361), which waveguide (338) extends through. As best seen in FIGS. 10A-10C, tubular passage (361) is sized to accommodate the outer diameter of waveguide (338) such that waveguide (338) does not contact the inner surface of cap (362) when waveguide (338) mechanically oscillates.

Longitudinally extending arm (364) is substantially similar to longitudinally extending arm (264) described above, with differences described below. Therefore, longitudinally extending arm (364) unitarily extends from cap (362) along the length of ultrasonic blade (342). As best shown in FIGS. 11A-11C, longitudinally extending arm (364) defines a hollow or concave pathway (365) that houses a portion of ultrasonic blade (342). In particular, longitudinally extending arm (364) may house ultrasonic blade (342) so that the portion of ultrasonic blade (342) facing toward clamp pad (366) is exposed while the portion of ultrasonic blade (342) facing away from clamp pad (366) is confined within longitudinally extending arm (364). As will be described in greater detail below, longitudinally extending arm (364) may act as a heat guard for ultrasonic blade (342).

Concave pathway (365) of longitudinally extending arm (354) is dimensioned to form a gap between the outer diameter of ultrasonic blade (342) and the inner surface of longitudinally extending arm (354) defining concave pathway (365). The gap formed by concave pathway (365) is large enough so that ultrasonic blade (342) does not contact the inner surface of longitudinally extending arm (354) when ultrasonic blade (342) mechanically oscillates. This may prevent unwanted contact between ultrasonic blade (342) and blade guard (360).

Resiliently flexible guard tine (368) is positioned at the distal end of longitudinally extending arm (264). Resiliently flexible guard tine (368) is made out of a material that is sufficiently resilient to allow tine (368) to flex relative to longitudinally extending arm (364) in response to an external force; and to allow tine (368) to return to an unaltered position when the external force is no longer applied.

Resiliently flexible guard tine (368) comprises a laterally extending body (367) and a grasping surface (349). Laterally extending body (347) projects laterally away from the longitudinal axis defined by ultrasonic blade (342), although this is merely optional. The offset position of laterally extending body (367) relative to the longitudinal axis defined by ultrasonic blade (342) may allow an operator to better visualize guard tine (368) during use of end effector (340). Grasping surface (369) of guard tine (368) forms a flat surface facing at an oblique angle toward grasping surface (349) of clamp tine (348). While in the current example, grasping surface (369) forms a flat surface, this is merely optional. For instance, grasping surface (369) may include a plurality of ridges, an include surface, a waved surface, a knurled surface, or may have any other suitable geometry as would be apparent to one having ordinary skill in the art in view of the teachings herein.

FIGS. 10A-11C show end effector (340) transition from an open configuration (FIGS. 10A and 11A) to a first closed configuration (FIGS. 10B and 11B), and further to a second closed configuration (FIGS. 10C and 11C). As mentioned above, and as shown in FIGS. 11A-11B, grasping surface (369) of guard tine (368) forms an oblique angle with grasping surface (349) of clamp tine (348) when guard tine (368) is in an unaltered position. When an operator closes end effector (340) to the first closed configuration, as shown from FIGS. 10A-10B and 11A-11B, the free end of guard tine (368) not attached to longitudinally extending arm (364) is positioned to first make contact with grasping surface (349) of clamp tine (348). The contact between the free end of guard tine (368) and grasping surface (349) enables grasping and/or manipulation of tissue between grasping surfaces (349, 369). The operator may either move instrument (100) in order to move grasped tissue or further rotate tines (348, 368) together in order to form a blunt dissection. However, dimensioning tines (348, 368) to form a blunt dissection by further rotating tines (348, 368) is merely optional.

As described above, resiliently flexible guard tine (368) is made out of a material that flexes relative to longitudinally extending arm (364) in response to an external force. As shown in FIGS. 10C and 11C, the operator may further rotate clamp arm (344) toward ultrasonic blade (342) such that clamp tine (348) imparts an external force on guard tine (368), thereby flexing tine (368) relative to longitudinally extending arm (364). As grasping surfaces (349, 369) transition from the configuration shown in FIGS. 10B and 11B to the configuration shown in FIGS. 10C and 11C, grasping surfaces (349, 369) progressively deflect such that initially just the distal tips contact tissue; yet eventually, entire grasping surfaces (349, 369) are involved in grasping tissue. Grasping surfaces (349, 369) are then positioned so that end effector (340) is now located in its second closed configuration. In the second closed configuration, ultrasonic blade (342) is positioned a sufficient distance from clamp pad (346) to allow the operator to capture tissue between ultrasonic blade (342) and clamp pad (346) with the force required to cut through and seal tissue with activated ultrasonic blade (342). Therefore, the operator may choose between either performing a blunt dissection (or simply grasping tissue) or operating on tissue with an active ultrasonic blade (342) based on the closed configuration end effector (340).

While the current example utilizes resiliently flexible material in order to enable tine (368) to rotate in order to accomplish multiple closed configurations, any other suitable configuration may be used in order to allow tine (368) to rotate in response to an external force as would be apparent to one having ordinary skill in the art in view of the teachings herein. For example, a torsion spring may be provided within cap (362), enabling cap (362) and therefore tine (368) to rotate relative to blade (361) when an external force is applied to tine (368). The torsion spring or other resilient element may further allow cap (362) and therefore tine (368) to return to position when the external force is removed from tine (368).

While the current example shows tine (368) deflecting about the longitudinal axis defined by ultrasonic blade (342) due to the free end of tine (368) first making contact with clamp tine (348), tine (368) may be positioned to rotate about any other suitable axis as would be apparent to one having ordinary skill in the art in view of the teachings herein. For example, tine (368) may deflect about an axis that is perpendicular to the longitudinal axis defined by ultrasonic blade (342) due to a distal end of tine (368) first making contact with clamp tine (348). In some such versions, tine (368) extends its effective length longitudinally as tine (368) deflects.

While in the current example tine (368) is solely configured to deflect, clamp tine (348) may be configured to deflect alone or in combination with guard tine (368).

Additionally, the operator may manipulate tissue by transitioning end effector (340) from a closed configuration (FIG. 10B or 10C) to an open configuration (FIG. 10A). In particular, the operator may insert end effector (340) in a closed configuration between two organs or anatomical parts that are attached and/or stuck together. Once end effector (340) is placed in the desired location, the operator may open end effector (340) to separate the two organs or anatomical parts without exposing ultrasonic blade (342) to the targeted structures. In other words, clamp arm (344) and blade guard (360) may sufficiently shield ultrasonic blade (342) from tissue while end effector (340) is in a closed configuration such that end effector (340) may be inserted between two organs or anatomical parts in a closed configuration without imparting undesired heat to the tissue. Subsequently, end effector (340) may transition to an opened configuration so that the outer surface of blade guard (360) and the outer surface of clamp arm (344) make contact with the desired anatomical structure without unwanted contact between tissue and ultrasonic blade (342).

C. End Effector with Dual Stage Closure and Resilient Blade Guard

FIGS. 12A-13C show another alternative end effector (440) that may be readily incorporated into ultrasonic surgical instrument (100) described above. While end effector (340) is configured to transition from a first closed configuration to a second closed configuration based on flexing of guard tine (368), as shown in FIGS. 11B-11C, end effector (440) is configured to transition from a first closed configuration, as shown in FIGS. 12B and 13B, to a second closed configuration, as shown in FIGS. 12C and 13C. As will be described in greater detail below, the first closed configuration may allow an operator to passively grasp and/or manipulate desired tissue while the second closed configuration may allow the operator to capture tissue between an ultrasonic blade and a clamp pad with sufficient force required to cut through and seal tissue with an activated ultrasonic blade.

End effector (440) of this example comprises an ultrasonic blade (442), a clamp arm (444), and a blade guard (460) secured to the distal end of sheath (132). Ultrasonic blade (442) is integrally connected to a waveguide (438). Ultrasonic blade (442) and waveguide (438) are substantially similar to ultrasonic blade (142, 242, 342) and waveguide (138, 238, 338) described above. Therefore, waveguide (438) may communicate ultrasonic vibrations to ultrasonic blade (442).

Clamp arm (444) includes a clamp pad (446) facing ultrasonic blade (442).

Clamp arm (444) is substantially similar to clamp arm (244, 344) described above while clamp pad (446) is substantially similar to clamp pad (246, 346) described above, with differences described below. Therefore, clamp arm (444) is an integral feature of clamp arm assembly (150). Additionally, clamp arm (444) is pivotable toward and away from ultrasonic blade (442) based on pivoting of thumb grip ring (154) toward and away from body (133) of handle assembly (120).

A clamp tine (448) is positioned at the distal end of clamp arm (444). Clamp tine (448) comprises a laterally extending body (447) and a grasping surface (449). Laterally extending body (447) projects laterally away from the longitudinal axis defined by ultrasonic blade (442), although this is merely optional. The offset position of laterally extending body (447) relative to the longitudinal axis defined by ultrasonic blade (442) may allow an operator to better visualize clamp tine (448) during use of end effector (440). Grasping surface (449) includes a flat planar surface in this example, however it should be understood that the flat planar surface is merely optional. For instance, grasping surface (449) may comprise a plurality of ridges, an inclined surface, a waved surface, a knurled surface, or have any other suitable geometry as would be apparent to one having ordinary skill in the art in view of the teachings herein. As will be described in greater detail bellow, clamp tine (448) is configured to rotate with clamp arm (444) toward and away from blade guard (460) to passively grasp and/or perform blunt dissections on targeted tissue.

Blade guard (460) comprises a cap (462), a resiliently flexible longitudinal extending arm (464), and a resiliently flexible guard tine (468). Cap (462) is substantially similar to cap (262, 362) as described above. Therefore, cap (462) is secured to the distal end of sheath (132). Additionally, cap (462) defines a tubular passage (461), which waveguide (438) extends through. As best seen in FIGS. 12A-12C, tubular passage (461) is sized to accommodate the outer diameter of waveguide (438) such that waveguide (438) does not contact the inner surface of cap (462) when waveguide (438) mechanically oscillates.

Resiliently flexible longitudinally extending arm (464) is substantially similar to longitudinally extending arm (264, 364) described above, with differences described below. Resiliently flexible longitudinally extending arm (464) is made out of a material that is sufficiently resilient to flex relative to cap (462) in response to an external force; and to return to an unaltered position when the external force is no longer applied.

Longitudinally extending arm (464) extends from cap (462) along the length of ultrasonic blade (442). As best shown in FIGS. 13A-13C, longitudinally extending arm (464) defines a hollow or concave pathway (465) that houses a portion of ultrasonic blade (442). In particular, longitudinally extending arm (464) may house ultrasonic blade (442) so that the portion of ultrasonic blade (442) facing toward clamp pad (466) is exposed while the portion of ultrasonic blade (442) facing away from clamp pad (466) is confined within longitudinally extending arm (464). As will be described in greater detail below, longitudinally extending arm (464) may act as a heat guard for ultrasonic blade (442).

Concave pathway (465) of longitudinally extending arm (454) is dimensioned to form a gap between the outer diameter of ultrasonic blade (442) and the inner surface of longitudinally extending arm (454) defining concave pathway (465). The gap formed by concave pathway (465) is large enough so that ultrasonic blade (442) does not contact the inner surface of longitudinally extending arm (454) when ultrasonic blade (442) mechanically oscillates. This may prevent unwanted contact between ultrasonic blade (442) and blade guard (460).

Guard tine (468) is positioned at the distal end of longitudinally extending arm (464). Guard tine (468) comprises a laterally extending body (467) and a grasping surface (449). Laterally extending body (447) projects laterally away from the longitudinal axis defined by ultrasonic blade (442), although this is merely optional. The offset position of laterally extending body (467) relative to the longitudinal axis defined by ultrasonic blade (442) may allow an operator to better visualize guard tine (468) during use of end effector (440). Grasping surface (469) of guard tine (468) forms a flat surface facing toward grasping surface (449) of clamp tine (448). While in the current example, grasping surface (469) forms a flat surface, this is merely optional. For instance, grasping surface (469) may include a plurality of ridges, an include surface, a waved surface, a knurled surface, or have any other suitable geometry as would be apparent to one having ordinary skill in the art in view of the teachings herein.

It should be understood that laterally extending body (467) of guard tine (468) extends in the same general direction of laterally extending body (447) of clamp tine (448). Grasping surface (469) of guard tine (468) and grasping surface (449) of clamp tine (448) at least partially align in both longitudinal and lateral directions while end effector (440) is in either the first closed configuration (FIGS. 12B and 13B) or the second closed configuration (FIGS. 12C and 13C). In other words, grasping surfaces (449, 469) are positioned so that rotation of clamp arm (444) toward ultrasonic blade (442) will cause contact between grasping surfaces (449, 469) to enable grasping and/or manipulation of tissue between grasping surfaces (449, 469). As will be described in greater detail below, this may allow for grasping surfaces (449, 469) to interact with each other in order to passively grasp or passively sever tissue captured between grasping surfaces (449, 469) when clamp arm (444) rotates toward ultrasonic blade (442).

FIGS. 12A-13C show end effector (440) transition from an open configuration (FIGS. 12A and 13A) to a first closed configuration (FIGS. 12B and 13B), and further to a second closed configuration (FIGS. 12C and 13C). When an operator closes end effector (440) to the first closed configuration, as shown from FIGS. 12A-12B and 13A-13B, grasping surfaces (449, 469) align to grasp tissue. The operator may either move instrument (100) in order to move grasped tissue or further rotate tines (448, 468) together in order to form a blunt dissection. However, dimensioning tines (448, 468) to form a blunt dissection by further rotating tines (448, 468) is merely optional.

As described above, resiliently flexible longitudinally extending arm (464) is made out of a material that flexes relative to cap (462) in response to an external force. As shown in FIGS. 12C and 13C, an operator may further rotate clamp arm (444) toward ultrasonic blade (442) such that clamp tine (448) imparts an external force on guard tine (468) and longitudinally extending arm (464), thereby flexing arm (464) relative to cap (462). End effector (440) is now located in the second closed configuration. In the second closed configuration, ultrasonic blade (442) is positioned a sufficient distance from clamp pad (446) to allow the operator to capture tissue between ultrasonic blade (442) and a clamp pad (446) with the force required to cut through and seal tissue with activated ultrasonic blade (442). Therefore, an operator may choose between either performing a blunt dissection (or simply grasping tissue) or operating on tissue with an active ultrasonic blade (442) based on the closed configuration end effector (440).

It should be understood that concave pathway (465) is dimensioned to that resiliently flexible longitudinally extending arm (464) does not make contact with activated ultrasonic blade (442) while end effector (440) is in the second closed configuration.

Additionally, an operator may manipulate tissue by transitioning end effector (440) from a closed configuration (FIG. 12B or 12C) to an open configuration (FIG. 12A). For instance, the operator may insert end effector (440) in a closed configuration between two organs or anatomical parts that are attached and/or stuck together. Once end effector (440) is placed in the desired location, the operator may open end effector (440) to separate the two organs or anatomical parts without exposing ultrasonic blade (442) to the targeted structures. In other words, clamp arm (444) and blade guard (460) may sufficiently shield ultrasonic blade (442) from tissue while end effector (440) is in a closed configuration such that end effector (440) may be inserted between two organs or anatomical parts in a closed configuration without imparting undesired heat to the tissue. Subsequently, end effector (440) may transition to an opened configuration so that the outer surface of blade guard (460) and the outer surface of clamp arm (444) make contact with the desired anatomical structure without unwanted contact between tissue and ultrasonic blade (442).

D. End Effector with Dual Stage Closure and Resilient Ultrasonic Blade

FIGS. 14A-15C show another alternative end effector (540) that may be readily incorporated into ultrasonic surgical instrument (100) described above. While end effector (340, 440) is configured to transition from a first closed configuration associated with grasping and/or manipulating tissue with tines (348, 368, 448, 468) to a second closed configuration associated with cutting through and sealing tissue with an activated ultrasonic blade (342, 442), end effector (540) of the present example is configured to transition from a first closed configuration (associated with cutting through and sealing tissue with an activated ultrasonic blade) to a second closed configuration (associated with grasping and/or manipulating tissue with tines).

End effector (540) of this example comprises a resiliently flexible ultrasonic blade (542), a clamp arm (544), and a blade guard (560) secured to the distal end of sheath (132). Ultrasonic blade (542) is integrally connected to a resilient flexible waveguide (538). Ultrasonic blade (542) and waveguide (538) are substantially similar to ultrasonic blade (142, 242, 342, 442) and waveguide (138, 238, 338, 438) described above, with differences elaborated below. Therefore, waveguide (538) may communicate ultrasonic vibrations to ultrasonic blade (542).

Resiliently flexible waveguide (538) and resiliently flexible ultrasonic blade (542) are made out of a material having sufficient resilience such that blade (542) flexes relative to outer sheath (132) in response to an external force; and returns to an unaltered position when the external force is no longer applied.

Clamp arm (544) includes a clamp pad (546) facing ultrasonic blade (542). Clamp arm (544) is substantially similar to clamp arm (244, 344, 444) described above while clamp pad (546) is substantially similar to clamp pad (246, 346, 446) described above, with differences described below. Therefore, clamp arm (544) is an integral feature of clamp arm assembly (150). Additionally, clamp arm (544) is pivotable toward and away from ultrasonic blade (542) based on pivoting of thumb grip ring (154) toward and away from body (133) of handle assembly (120).

A clamp tine (548) is positioned at the distal end of clamp arm (544). Clamp tine (548) comprises a laterally extending body (547) and a grasping surface (549). Laterally extending body (547) projects laterally away from the longitudinal axis defined by ultrasonic blade (542), although this is merely optional. The offset position of laterally extending body (547) relative to the longitudinal axis defined by ultrasonic blade (542) may allow an operator to better visualize clamp tine (548) during use of end effector (540). Grasping surface (549) includes a flat planar surface in this example, however it should be understood that the flat planar surface is merely optional. For instance, grasping surface (549) may comprise a plurality of ridges, an inclined surface, a waved surface, a knurled surface, or have any other suitable geometry as would be apparent to one having ordinary skill in the art in view of the teachings herein. As will be described in greater detail bellow, clamp tine (548) is configured to rotate with clamp arm (544) toward and away from blade guard (560) to passively grasp and/or perform blunt dissections on targeted tissue.

Blade guard (560) comprises a cap (562), a longitudinally extending arm (564) and a resiliently flexible guard tine (568). Cap (562) is substantially similar to cap (262, 362, 462) as described above. Therefore, cap (562) is secured to the distal end of sheath (132). Additionally, cap (562) defines a tubular passage (561), which waveguide (538) extends through. As best seen in FIGS. 14A-14C, tubular passage (561) is sized to accommodate the outer diameter of waveguide (538) such that waveguide (538) does not contact the inner surface of cap (562) when waveguide (538) mechanically oscillates.

Longitudinally extending arm (564) is substantially similar to longitudinally extending arm (264, 364) described above. Longitudinally extending arm (564) extends from cap (562) along the length of ultrasonic blade (542). As best shown in FIGS. 15A-15C, longitudinally extending arm (564) defines a hollow or concave pathway (565) that houses a portion of ultrasonic blade (542). In particular, longitudinally extending arm (564) may house ultrasonic blade (542) so that the portion of ultrasonic blade (542) facing toward clamp pad (566) is exposed while the portion of ultrasonic blade (542) facing away from clamp pad (566) is confined within longitudinally extending arm (564). As will be described in greater detail below, longitudinally extending arm (564) may act as a heat guard for ultrasonic blade (542).

Concave pathway (565) of longitudinally extending arm (454) is dimensioned to form a gap between the outer diameter of ultrasonic blade (542) and the inner surface of longitudinally extending arm (554) defining concave pathway (565). The gap formed by concave pathway (565) is large enough so that ultrasonic blade (542) does not contact the inner surface of longitudinally extending arm (554) when ultrasonic blade (542) mechanically oscillates. This may prevent unwanted contact between ultrasonic blade (542) and blade guard (560).

Guard tine (568) is positioned at the distal end of longitudinally extending arm (564). Guard tine (568) comprises a laterally extending body (567) and a grasping surface (549). Laterally extending body (547) projects laterally away from the longitudinal axis defined by ultrasonic blade (542), although this is merely optional. The offset position of laterally extending body (567) relative to the longitudinal axis defined by ultrasonic blade (542) may allow an operator to better visualize guard tine (568) during use of end effector (540). Grasping surface (569) of guard tine (568) forms a flat surface facing toward grasping surface (549) of clamp tine (548). While in the current example, grasping surface (569) forms a flat surface, this is merely optional. For instance, grasping surface (569) may include a plurality of ridges, an include surface, a waved surface, a knurled surface, or have any other suitable geometry as would be apparent to one having ordinary skill in the art in view of the teachings herein.

It should be understood that laterally extending body (567) of guard tine (568) extends in the same general direction of laterally extending body (547) of clamp tine (548). Grasping surface (569) of guard tine (568) and grasping surface (549) of clamp tine (548) at least partially align in both longitudinal and lateral directions while end effector (540) is in the second closed configuration, as shown in FIGS. 14C and 15C. In other words, grasping surfaces (549, 569) are positioned so that rotation of clamp arm (544) toward ultrasonic blade (542) will cause contact between grasping surfaces (549, 569) to enable grasping and/or manipulation of tissue between grasping surfaces (549, 569). As will be described in greater detail below, this may allow for grasping surfaces (549, 569) to interact with each other in order to passively grasp or passively sever tissue captured between grasping surfaces (549, 569) when clamp arm (544) rotates toward ultrasonic blade (542).

FIGS. 14A-15C show end effector (440) transition from an open configuration (FIGS. 14A and 15A) to a first closed configuration (FIGS. 14B and 15B), and further to a second closed configuration (FIGS. 14C and 15C). When an operator closes end effector (540) to the first closed configuration, as shown from FIGS. 14A-14B and 15A-15B, clamp pad (546) makes contact with ultrasonic blade (542) while tines (548, 568) are positioned to a predefined distance from one another. Ultrasonic blade (542) is positioned a sufficient distance from clamp pad (546) to allow the operator to capture tissue between ultrasonic blade (542) and clamp pad (546) with the force required to cut through and seal tissue with activated ultrasonic blade (542).

Grasping surfaces (449, 469) align to grasp tissue. The operator may either move instrument (100) in order to move grasped tissue or further rotate tines (448, 468) together in order to form a blunt dissection.

As described above, ultrasonic blade (542) and waveguide (538) are made out of a material that flexes relative to outer sheath (132) in response to an external force. As shown in FIGS. 14C and 15C, the operator may further rotate clamp pad (546) against ultrasonic blade (542) such that clamp pad (546) imparts an external force on ultrasonic blade (542) and waveguide (538), thereby flexing ultrasonic blade (542) and waveguide (538) relative to outer sheath (132). Grasping surfaces (549, 569) are now positioned relative to each other in order to grasp tissue. An operator may either move instrument (100) in order to move grasped tissue or further rotate tines (548, 568) together in order to perform a blunt dissection. Therefore, an operator may choose between either performing a blunt dissection (or simply grasping tissue) or operating on tissue with an active ultrasonic blade (542) based on the closed configuration end effector (540).

Some versions, ultrasonic blade (542) and waveguide (538) are formed of a material that flexes relative to outer sheath (132) in response to a perpendicularly directed external force of sufficient magnitude. In addition or in the alternative, other elements connected to waveguide (538) may be configured to flex relative to outer sheath (132) in response to an external force. Such other elements may be configured to flex or deform in response to external forces that are of a lower magnitude than the forces required to flex ultrasonic blade (542) and waveguide (538). For example, a seal (590) made of elastomeric material, positioned about waveguide (538) in outer sheath (132), could deform in response to an external force. Thus, the same effect as shown in FIGS. 14B-14C and FIGS. 15B-15C could occur due to deformation of seal (590) rather than deformation of blade (542) or waveguide (538). By way of example only, such a seal (590) may be constructed and positioned in accordance with the teachings relating to "seal 83" in U.S. Pub. No. 2007/0191713, now abandoned, the disclosure of which is incorporated by reference herein.

Additionally, an operator may manipulate tissue by transitioning end effector (540) from a closed configuration (FIG. 14B or 14C) to an open configuration (FIG. 14A). The operator may insert end effector (540) in a closed configuration between two organs or anatomical parts that are attached and/or stuck together. Once end effector (540) is placed in the desired location, the operator may open end effector (540) to separate the two organs or anatomical parts without exposing ultrasonic blade (542) to the targeted structures. In other words, clamp arm (544) and blade guard (560) may sufficiently shield ultrasonic blade (542) from tissue while end effector (540) is in a closed configuration such that end effector (540) may be inserted between two organs or anatomical parts in a closed configuration without imparting undesired heat to the tissue. Subsequently, end effector (540) may transition to an opened configuration so that the outer surface of blade guard (560) and the outer surface of clamp arm (544) make contact with the desired anatomical structure without unwanted contact between tissue and ultrasonic blade (542).

III. Exemplary Instrument with Safety Switch for Two Stage Closure

In some instances it may be desirable to provide a safety switch that allows an operator to activate an ultrasonic blade when the distance between ultrasonic blade and clamp pad is sufficient to provide the compression required to effectively cut through and seal tissue with an activated ultrasonic blade. This may be useful with an instrument having two stage closure where the first closed configuration allows an operator to passively grasp and/or manipulate desired tissue while the second closed configuration allows an operator to capture tissue between an ultrasonic blade and a clamp pad with sufficient compression force to cut through and seal tissue with an activated ultrasonic blade, similar to end effectors (240, 340) described above.

FIGS. 16A-16B show an instrument (200) including a transducer assembly (212), a handle assembly (220), a shaft assembly (230), and clamp arm assembly (250); which are substantially similar to transducer assembly (112), handle assembly (120), shaft assembly (130), and clamp arm assembly (150) as described above, respectively, with differences described below. Instrument (200) also includes end effector (240) as described above. As described above, end effector (240) has two closure configurations, including a first closed configuration that allows an operator to passively grasp and/or manipulate desired tissue and a second closed configuration that allows an operator to capture tissue between ultrasonic blade (242) and clamp pad (246) with sufficient force to cut through and seal tissue with activated ultrasonic blade (242).

Handle assembly (220) include a body (224), a finger grip (224), and a pair of buttons (226) that are substantially similar to handle assembly (120), finger grip (124), and buttons (126) as described above, respectively, with differences described below. Buttons (226) are configured to activate ultrasonic blade (242) of end effector (240).

Shaft assembly (230) includes an outer sheath (232) and a first switch element (282). Outer sheath (232) is substantially similar to outer sheath (132) as described above. As will be described in greater detail below, first switch element (282) is configured to prevent buttons (226) from activating ultrasonic blade (242) when first switch element (282) is not in contact with a second switch element (280). First switch element (282) is also configured to allow buttons (226) to activate ultrasonic blade (242) when in contact with second switch element (280).

Clamp arm assembly (250) includes thumb grip (254), shank (252), and second switch element (280). Thumb grip (254) and shank (252) are substantially similar to thumb grip (154) and shank (152) described above, with differences described below. Pin (256) pivotally couples clamp arm assembly (250) with outer sheath (232) of shaft assembly (230).

As seem in FIGS. 16A-16C, second switch element (280) is located on shank (252) such that as clamp arm assembly (250) pivots toward body (222), second switch element (280) pivots toward first switch element (282). FIG. 16A depicts end effector (240) in a position corresponding to FIGS. 10A and 11A. Therefore, end effector (240) is in an open configuration in FIG. 16A. It should be understood that if an operator attempts to press buttons (226) with end effector (240) in the open configuration of FIG. 16A, ultrasonic blade (242) of end effector (240) will not activate because first switch element (282) is not in contact with second switch element (280).

FIG. 16B depicts end effector (240) in a position corresponding to FIGS. 10B and 11B. Therefore, end effector (240) is in the first closed configuration in FIG. 16B. At this point, end effector (240) is capable of grasping tissue or manipulating tissue with tines (248, 268). However, clamp pad (246) and ultrasonic blade (242) are not close enough such that activation of ultrasonic blade (242) would cut and seal tissue captured between clamp pad (246) and ultrasonic blade (242). It should be understood that if an operator attempts to press buttons (226), ultrasonic blade (242) of end effector (240) will not activate because first switch element (282) is still not yet in contact with second switch element (280).

FIG. 16C depicts end effector (240) in a position corresponding to FIGS. 10C and 11C. Therefore, end effector (240) is in the second closed configuration in FIG. 16C. At this point, end effector (240) is capable of capturing tissue between clamp pad (246) and ultrasonic blade (242) with sufficient compression force such that activation of ultrasonic blade (242) would cut and seal tissues captured between clamp pad (246) and ultrasonic blade (242). It should be understood that first switch element (282) and second switch element (280) are now in contact with each other. Therefore, ultrasonic blade (242) will be ultrasonically activated when the operator presses either button (226) at this stage.

It should be understood from the foregoing that first switch element (282) and second switch element (280) ensure that when an operator presses buttons (226) to activate ultrasonic blade (242), there is sufficient compression force provided between clamp pad (246) and ultrasonic blade (242). It should also be understood that end effector (340) or any other suitable end effector with two stage closure may be utilized with instrument (200) in replacement of end effector (240).

IV. Exemplary End Effector with Ultrasonic Blade Distal of Laterally Extending Tines In some instances, it may be desirable to have an end effector with an ultrasonic blade extending distally in relation to laterally extending tines. A portion of ultrasonic blade extending distally in relation to laterally extending tines may add more functionality. For instance, an operator may use such a distal portion of ultrasonic blade for otomy creation when the blade is energized.

FIGS. 17-19 show an exemplary end effector (640) that may be readily incorporated into instrument (100, 200) in place of end effector (140, 240). End effector (640) of this example includes an ultrasonic blade (642), a clamp arm (644), and a blade guard (660). Clamp arm (644) may be substantially similar to clamp arm (244, 344, 444, 544) described above. Clamp arm (644) includes clamp pad (646) and clamp tine (648), which may be substantially similar to clamp pad (246, 346, 446, 546) and clamp tine (248, 348, 448, 548), respectively described above. Therefore, clamp tine (648) includes a laterally extending body (647) and a grasping surface (649) that may be substantially similar to laterally extending body (247, 347, 447, 547) and grasping surface (249, 349, 449, 549), respectively described above.

Blade guard (660) includes a cap (662), a longitudinally extending arm (664) and a guard tine (668), which may be substantially similar to cap (262, 362, 462, 562), longitudinally extending arm (264, 364, 464, 564), and guard tine (268, 368, 468, 568), respectively, described above with differences described below. Therefore, guard tine (668) includes a laterally extending body (667) and a grasping surface (669), which may substantially similar to laterally extending body (267, 367, 467, 567) and grasping surface (269, 369, 496, 569), respectively described above, with difference described below. Additionally, longitudinally extending arm (664) defines a hollow or concave pathway (665) substantially similar to concave pathway (265, 365, 465, 565) described above.

Ultrasonic blade (642) may be substantially similar to ultrasonic blade (142, 242, 342, 442, 552) mentioned above, with differences described below. Ultrasonic blade (642) includes a distal end (643) extending distal in relation to guide tine (668). Guide tine (668) defines a distal opening (666) to accommodate distal end (643) of ultrasonic blade (642). It should be understood that distal opening (666) is dimensioned such that guide tine (668) does not contact ultrasonic blade (642) during mechanical oscillation of ultrasonic blade (642). Distal end (643) of ultrasonic blade (642) extends distally past the bend formed by guard tine (668), to a sufficient distance to allow distal end (643) of ultrasonic blade (642) to be inserted into a targeted anatomical structure in order to create an otomy in the anatomical structure when ultrasonic blade (642) is activated. Distal end (643) of ultrasonic blade (642) may also take on other functions, such as a scalpel or any other suitable function as would be apparent to one having ordinary skill in the art in view of the teachings herein.

It should be understood that end effector (640) may incorporate any of the closing features of end effector (240, 340, 440, 540) as would be apparent to one having ordinary skill in the art in view of the teachings herein. Therefore, distal opening (666) may be dimensioned to accommodate for any of the other features present in end effector (240, 340, 440, 540) without making contact with ultrasonic blade (642).

In some versions, ultrasonic blade (642) is retractable from a distal position, as shown in FIGS. 17-19, to a proximal position. When ultrasonic blade (642) is in the proximal position, distal end (643) of ultrasonic blade (642) is located within the confines of concave pathway (665). A slide switch or other actuator may be operable to selectively translate transducer assembly (112) and ultrasonic blade (642) distally to expose distal end (643) of ultrasonic blade (642) past distal opening (666). The same slide switch or actuator may be operable to selectively translate transducer assembly (112) and ultrasonic blade (642) proximally to retract distal end (643) of ultrasonic blade (642) back into distal opening (666). Various suitable components, configurations, and techniques that may be used to provide longitudinal translation of transducer assembly (112) and ultrasonic blade (642), to selectively expose and conceal distal end (643), will be apparent to those of ordinary skill in the art in view of the teachings herein.

V. Exemplary Instrument with Two Independent Tines

In some instances, it may be desirable to have two tines that are both pivotable relative to ultrasonic blade (142). FIGS. 20-21B show an exemplary instrument (700) that provides such functionality. Instrument (700) includes a handle assembly (720), a shaft assembly (730), end effector (740), and a clamp arm assembly (750). A transducer assembly (712) is fixed to body (722). Handle assembly (720) and transducer assembly (712) are substantially similar to handle assembly (120) and transducer assembly (112) described above, with differences described below.

Handle assembly (120) includes a body (722) including a body finger grip (724), a body thumb grip (728), and a pair of buttons (726). Buttons are substantially similar to buttons (126) described above. Shaft assembly (730) includes an outer sheath (732). Clamp arm assembly (750) includes a first shank (752) unitarily connected to a thumb grip ring (754), and a second shank (772) unitarily connected to a shank finger grip (774). First shank (752) and second shank (772) are pivotally connected to shaft assembly (730) and handle assembly (720) via a pin (756). Therefore, an operator may pivot first shank (752) and second shank (772) relative to handle assembly (722).

End effector (740) includes an ultrasonic waveguide (738) unitarily connected to an ultrasonic blade (742), which are substantially similar to ultrasonic waveguide (138) and ultrasonic blade (142) described above. Therefore, an operator may press buttons (726) in order to activate transducer assembly (712), which generates ultrasonic vibrations that travel through ultrasonic waveguide (738) to ultrasonic blade (742). Ultrasonic waveguide (738) extends distally from outer sheath (732).

End effector (740) also includes a clamp arm (744) integrally connected to first shank (752) and extending distally from pin (756). Therefore, an operator may pivot first shank (752) toward body (722), which in turn pivots clamp arm (744) toward ultrasonic blade (742). Clamp arm (744) includes a clamp pad (746) and a first tine (748). Clamp pad (746) may be substantially similar to clamp pad (226) described above. First tine (748) includes a laterally extending body (748) and a grasping surface (749), which are substantially similar to laterally extending body (248) and grasping surface (249), respectively. In some alternative versions, first tine (748) is omitted.

End effector (740) also includes a clamp arm (764) integrally connected to second shank (772) and extending distally from pin (756). Therefore, an operator may pivot second shank (772) toward body (722), which in turn pivots clamp arm (764) toward ultrasonic blade (742). Clamp arm (764) includes a clamp pad (766) and a second tine (768). Second tine (768) includes a laterally extending body (767) and a grasping surface (769) which mirror laterally extending body (747) and grasping surface (749) of first tine (748). In some alternative versions, second tine (768) is omitted.

As seen in from FIGS. 21A-21B, an operator may grasp shank thumb grip (754) and shank finger grip (774) in order to pivot first tine (748) and second tine (768) toward each other. Grasping surfaces (749, 769) may then pivot close enough in order grasp; or grasping surfaces (749, 769) may pivot further in order to for a blunt dissection. First tine (748) and second tine (768) may be indexed relative to one another through a gear and/or other component(s), such that both tines (748, 768) close symmetrically relative to each other. Various suitable components, configurations, and techniques that may be used to provide such indexing method will be apparent to one having ordinary skill in the art in view of the teachings herein.

An operator may also pivot either first shank (752) or second shank (772) toward body (722) in order to capture tissue between ultrasonic blade (742) and either clamp pad (746, 766) respectively. An operator may then press buttons (726) in order to cut and seal tissue captured between ultrasonic blade (742) and either clamp pad (746, 766)

respectively. Body thumb grip (728) and body finger grip (724) are provided for an operator to grasp depending on which shank (752, 772) an operator decides to utilize in order to grasp tissue between ultrasonic blade (742) and either clamp pad (746, 766) respectively. For instance, if an operator decides to grasp tissue between first clamp arm (744) and ultrasonic blade (742), an operator may place their thumb in shank thumb grip (754) and their finger in body finger grip (724) in order to pivot first shank (752) toward body (722).

It should be understood that grip (724) may be configured to engage grip (774) when shank (772) completes a full range of motion during closure of clamp arm (764) toward blade (742). In other words, grip (724) may arrest motion of clamp arm (764) toward blade (742) when grip (774) engages blade (742). Similarly, grip (728) may be configured to engage grip (754) when shank (752) completes a full range of motion during closure of clamp arm (744) toward blade (742). In other words, grip (728) may arrest motion of clamp arm (744) toward blade (742) when grip (754) engages blade (742). Alternatively, grips (724, 728) may be configured or positioned such that grips (754, 774) do not engage grips (724, 728). In some versions, grips (724, 728) are simply omitted.

It should also be understood from the foregoing that an operator may choose between either performing a blunt dissection (or simply grasping tissue) or operating on tissue with an active ultrasonic blade (742) with one single end effector (740).

In some instances, it may be desirable to make tines (248, 268, 348, 368, 448, 468, 548, 568, 648, 668, 748, 768) removable and replaceable from the rest of end effector (240, 340, 440, 540, 640, 740) respectively. This way, an operator may choose tines (248, 268, 348, 368, 448, 468, 548, 568, 648, 668, 748, 768) with different geometries as discussed above, based on whichever geometry best suits the surgical operation at hand. Additionally, tines (248, 268, 348, 368, 448, 468, 548, 568, 648, 668, 748, 768) may be removed and replaced during a surgical operation that requires grasping tissue at multiple locations, which may not necessarily be completed easily by a single set of tines (248, 268, 348, 368, 448, 468, 548, 568, 648, 668, 748, 768).

Additionally, or alternatively, tines (248, 268, 348, 368, 448, 468, 548, 568, 648, 668, 748, 768) may be made of a low thermal conduction material, such as ceramic. This may allow end effector (240, 340, 440, 540, 640, 740) to apply bipolar RF energy to a surgical site such that tines (248, 268, 348, 368, 448, 468, 548, 568, 648, 668, 748, 768) would be non-conductive both thermally and electrically.

Additionally, or alternatively, a leaf spring or other resilient biasing mechanism may be placed behind clamp pad (246, 346, 446, 546, 646, 756, 766) to ensure that clamp pad (246, 346, 446, 546, 646, 756, 766) applies the appropriate force as well as deflect when tines (248, 268, 348, 368, 448, 468, 548, 568, 648, 668, 748, 768) rotate toward each other to a closed configuration. By way of example only, such a resilient biasing mechanism may be provided in accordance with at least some of the teachings of U.S. Pub. No. 2015/0148834, entitled "Ultrasonic Surgical Instrument with Staged Clamping," published May 28, 2015, issued as U.S. Pat. No. 10,004,527 on Jun. 26, 2018 the disclosure of which is incorporated by reference herein.

Additionally, or alternatively, concave pathway (265, 365, 465, 565, 665, 765) may further define a slot in order to allow blade (242, 342, 442, 542, 642, 742) to further deflect more easily while also avoiding contact between blade (242, 342, 442, 542, 642, 742) and longitudinally extending arm (264, 364, 464, 564, 664, 764).

Additionally, or alternatively, blade (242, 342, 442, 542, 642, 742) could have a curved profile while tines (248, 268, 348, 368, 448, 468, 548, 568, 648, 668, 748, 768) extend past blade (242, 342, 442, 542, 642, 742) along the same curved profile (e.g., on the same radius of curvature).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly; (c) an acoustic waveguide; and (d) an end effector comprising: (i) an ultrasonic blade in acoustic communication with the waveguide, (ii) a clamp arm configured to pivot toward and away from the ultrasonic blade, wherein the clamp arm comprises a first tine, and (iii) a blade guard extending from the shaft, wherein the blade guard comprises a longitudinally extending arm defining a concave pathway and a second tine located distal to the longitudinally extending arm; wherein the ultrasonic blade is partially housed within the concave pathway, wherein the first tine and the second tine are configured to grasp tissue when the clamp arm pivots toward the ultrasonic blade.

Example 2

The apparatus of Example 1, wherein the ultrasonic blade defines a longitudinal axis, wherein the first tine and the second tine extend transversely relative to the longitudinal axis.

Example 3

The apparatus of any one or more of Examples 1 through 2, wherein the first tine defines a plurality of ridges.

Example 4

The apparatus of any one or more of Examples 1 through 3, wherein the clamp arm further comprises a clamp pad facing the ultrasonic blade.

Example 5

The apparatus of any one or more of Examples 1 through 4, wherein the clamp arm is configured to pivot toward the ultrasonic blade from an open configuration to a first closed configuration, wherein the first tine and the second tine are configured to grasp tissue in the first closed configuration, wherein the clamp arm is configured to pivot further toward the ultrasonic blade from the first closed configuration to a second closed configuration, wherein the ultrasonic blade is configured to cut tissue in the second closed configuration.

Example 6

The apparatus of Example 5, wherein the blade guard is configured to flex when the clamp arm transitions from the first closed configuration to the second closed configuration.

Example 7

The apparatus of Example 6, wherein the second tine is configured to flex relative to the longitudinally extending arm when the clamp arm transitions from the first closed configuration to the second closed configuration.

Example 8

The apparatus of any one or more of Examples 6 through 7, wherein the longitudinally extending arm is configured to flex relative to the shaft when the clamp arm transitions from the first closed configuration to the second closed configuration.

Example 9

The apparatus of any one or more of Examples 6 through 8, wherein the concave pathway is dimensioned to prevent contact between the blade guard and the ultrasonic blade when the clamp arm is in the second closed configuration.

Example 10

The apparatus of any one or more of Examples 8 through 9, wherein the ultrasonic blade defines a longitudinal axis, wherein the longitudinally extending arm is configured to flex along the longitudinal axis when the clamp arm transitions from the first closed configuration to the second closed configuration.

Example 11

The apparatus of any one or more of Examples 5 through 10, wherein the apparatus further comprises a safety switch configured to selectively prevent activation of the ultrasonic blade.

Example 12

The apparatus of Example 11, wherein the safety switch is configured to selectively allow activation of the ultrasonic blade when the clamp arm is in the second closed configuration.

Example 13

The apparatus of any one or more of Examples 1 through 12, wherein the second tine defines a distal opening, wherein the ultrasonic blade extends from the concave pathway through the distal opening.

Example 14

The apparatus of any one or more of Examples 1 through 13, wherein the clamp arm is unitarily connected to a shank, wherein the shank is pivotally coupled to the shaft via a pin.

Example 15

The apparatus of any one or more of Examples 1 through 14, wherein the clamp arm is configured to pivot toward the ultrasonic blade from an open configuration to a first closed configuration, wherein the ultrasonic blade is configured to cut tissue in the first closed configuration, wherein the clamp arm is configured to pivot toward the ultrasonic blade from the first closed configuration to a second closed configuration, wherein the first tine and the second tine are configured to grasp tissue in the second closed configuration.

Example 16

The apparatus of Example 15, wherein the ultrasonic blade is configured to flex when the clamp arm pivots from the first closed configuration to the second closed configuration.

Example 17

An apparatus for operating on tissue, the apparatus comprising: (a) a body assembly; (b) a shaft extending distally from the body assembly; (c) an acoustic waveguide; and (d) an end effector comprising: (i) an ultrasonic blade in acoustic communication with the waveguide, (ii) a clamp arm comprising a first distal end and a clamp pad, wherein the clamp arm is configured to pivot toward and away the ultrasonic blade, wherein the clamp pad faces the ultrasonic blade, (iii) a blade guard extending from the shaft, wherein the blade guard comprises a second distal end, wherein the blade guard partially houses the ultrasonic blade, (v) a first tine attached to the first distal end of the clamp arm, wherein the first tine extends transversely relative to a longitudinal axis defined by the clamp arm, and (iv) a second tine attached to the second distal end of the blade guard, wherein the second tine extends transversely relative to a longitudinal axis defined by the blade guard; wherein the first tine and the second tine are configured to grasp tissue when the clamp arm pivots toward the ultrasonic blade.

Example 18

The apparatus of Example 17, wherein the blade guard is configured to flex in response to the clamp arm pivoting toward the ultrasonic blade.

Example 19

The apparatus of Example 18, wherein the second tine is configured to flex relative to the blade guard in response to the clamp arm pivoting toward the ultrasonic blade.

Example 20

An apparatus for operating on tissue, the apparatus comprising: (a) a body assembly; (b) a shaft extending distally from the body assembly; (c) an acoustic waveguide comprising a first side and a second side, wherein the first side is opposite the second side; and (d) an end effector comprising: (i) an ultrasonic blade in acoustic communication with the waveguide, (ii) a first clamp arm configured to pivot toward and away from the first side of the ultrasonic blade, wherein the clamp arm comprises a first tine, and (iii) a second clamp arm configured to pivot toward and away from the second side of the ultrasonic blade, wherein the second clamp arm comprises a second tine;

wherein the first tine and the second tine are configured to grasp tissue when the first clamp arm pivots toward the first side of the ultrasonic blade and the second clamp arm pivots toward the second side of the ultrasonic blade.

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument, comprising:
   (a) an acoustic waveguide; and
   (b) an end effector, including:
      (i) an ultrasonic blade in acoustic communication with the acoustic waveguide and distally extending from the acoustic waveguide,
      (ii) a clamp arm having a first tine with a first grasping surface extending along a first plane, wherein the clamp arm is configured to selectively move toward the ultrasonic blade from an open configuration for receiving a tissue to a closed configuration for compressing the tissue, and
      (iii) a blade guard positioned such that the ultrasonic blade is transversely between the blade guard and the clamp arm, wherein the blade guard includes:
         (A) a second tine having a second grasping surface extending along a second plane, and
         (B) a longitudinally extending arm defining a pathway such that the ultrasonic blade is received at least partially within the pathway, wherein at least a portion of the ultrasonic blade is positioned transversely below the second plane of the second grasping surface in the closed configuration, wherein the second tine is distally positioned relative to the longitudinally extending arm.

2. The surgical instrument of claim 1, wherein the closed configuration is a second closed configuration, and wherein the clamp arm is configured to selectively move from the open configuration toward the second closed configuration to a first closed configuration, wherein the first tine is engaged with the second tine in the first closed configuration for grasping the tissue therebetween.

3. The surgical instrument of claim 2, wherein the clamp arm is transversely closer to the ultrasonic blade in the second closed configuration than in the first closed configuration.

4. The surgical instrument of claim 2, wherein the second plane of the second grasping surface in the first closed configuration has a first orientation relative to the first plane of the first grasping surface, and wherein the second plane of the second grasping surface in the second closed configuration has a second orientation relative to the first plane of the first grasping surface.

5. The surgical instrument of claim 4, wherein at least a portion of the blade guard is configured to flex as the clamp arm transitions from the first closed configuration to the second closed configuration such that the second plane of the second grasping surface reorients from the first orientation to the second orientation.

6. The surgical instrument of claim 5, wherein the second tine is configured to flex relative to the longitudinally extending arm as the clamp arm transitions from the first closed configuration to the second closed configuration.

7. The surgical instrument of claim 5, wherein the second tine is resiliently flexible.

8. The surgical instrument of claim 5, wherein the second tine is configured to rotate such that the second grasping surface rotates from the first orientation to the second orientation.

9. The surgical instrument of claim 1, wherein the clamp arm further includes a clamp pad facing toward the ultrasonic blade.

10. The surgical instrument of claim 9, wherein the clamp pad is positioned transversely below the first plane of the first tine away from the ultrasonic blade.

11. The surgical instrument of claim 1, wherein the first tine has a first portion that laterally extends relative to the ultrasonic blade, and wherein the second tine has a second portion that laterally extends relative to the ultrasonic blade.

12. The surgical instrument of claim 1, wherein the longitudinally extending arm is unitarily formed with the blade guard.

13. A surgical instrument, comprising:
(a) an acoustic waveguide; and
(b) an end effector, including:
(i) an ultrasonic blade in acoustic communication with the acoustic waveguide,
(ii) a clamp arm having a first tine, and
(iii) a blade guard having a second tine,
wherein the clamp arm is configured to selectively move toward the ultrasonic blade from an open configuration and through a first closed configuration to a second closed configuration,
wherein the ultrasonic blade and clamp arm in the open configuration are configured to receive a tissue therebetween,
wherein the ultrasonic blade and clamp arm in the first closed configuration are positioned such that the ultrasonic blade is a first distance from the clamp arm and the first tine is engaged with the second tine,
wherein the ultrasonic blade and clamp arm in the second closed configuration are positioned such that the ultrasonic blade is a second distance from the clamp arm and the first tine is engaged with the second tine, and
wherein the first distance is greater than the second distance.

14. The surgical instrument of claim 13, wherein the blade guard is positioned such that the ultrasonic blade is transversely between the blade guard and the clamp arm.

15. The surgical instrument of claim 13, wherein the blade guard further includes a longitudinally extending arm defining a pathway such that the ultrasonic blade is received at least partially within the pathway.

16. The surgical instrument of claim 13, wherein the clamp arm is transversely closer to the ultrasonic blade in the second closed configuration than in the first closed configuration.

17. The surgical instrument of claim 13, wherein the second tine in the first closed configuration has a first orientation relative to the first tine, and wherein the second tine in the second closed configuration has a second orientation relative to the first tine.

18. The surgical instrument of claim 17, wherein at least a portion of the blade guard is configured to flex as the clamp arm transitions from the first closed configuration to the second closed configuration such that the second tine reorients from the first orientation to the second orientation.

19. A surgical instrument, comprising:
(a) an acoustic waveguide; and
(b) an end effector, including:
(i) an ultrasonic blade in acoustic communication with the acoustic waveguide,
(ii) a clamp arm, including:
(A) a clamp arm body having a longitudinally extending upper surface defining an arm body plane,
(B) a clamp pad secured to the longitudinally extending upper surface and facing toward the ultrasonic blade, and
(C) a first tine projecting from the clamp arm body and having a first grasping surface defining a first plane, wherein the clamp arm is configured to selectively move toward the ultrasonic blade from an open configuration for receiving a tissue to a closed configuration for compressing the tissue,
wherein the arm body plane is transversely recessed and offset from the first plane of the first grasping surface, and
(iii) a blade guard positioned such that the ultrasonic blade is transversely between the blade guard and the clamp arm, wherein the blade guard includes:
(A) a second tine, and
(B) a longitudinally extending arm defining a pathway such that the ultrasonic blade is received at least partially within the pathway,
wherein the first tine is configured to engage with the second tine in the closed configuration.

20. The surgical instrument of claim 19, wherein the clamp pad defines an upper pad surface facing toward the ultrasonic blade, and wherein the upper pad surface is recessed and offset from the first plane of the first grasping surface.

* * * * *